US008742199B2

(12) United States Patent
Roe et al.

(10) Patent No.: US 8,742,199 B2
(45) Date of Patent: *Jun. 3, 2014

(54) ABSORBENT ARTICLE HAVING DRYNESS INDICATING GRAPHIC

(71) Applicant: The Procter & Gamble Company, Cincinnati, OH (US)

(72) Inventors: Donald Carroll Roe, West Chester, OH (US); Thomas James Klofta, Cincinnati, OH (US); Mark John Ciesko, Hartland, WI (US); Barry Robert Feist, Madeira, OH (US); Kathleen Quinlan Ames-Ooten, Cincinnati, OH (US); Mathilde Clarisse Delhoume, Geneva (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/763,885

(22) Filed: Feb. 11, 2013

(65) Prior Publication Data

US 2013/0150816 A1    Jun. 13, 2013

Related U.S. Application Data

(62) Division of application No. 11/098,362, filed on Apr. 4, 2005, now Pat. No. 8,378,166.

(51) Int. Cl.
*A61F 13/42* (2006.01)

(52) U.S. Cl.
USPC .......................................... 604/361

(58) Field of Classification Search
USPC ................................ 604/361, 358
See application file for complete search history.

(56) References Cited

U.S. PATENT DOCUMENTS

| 3,675,654 A | 7/1972 | Baker |
| 3,860,003 A | 1/1975 | Buell |
| 4,022,211 A | 5/1977 | Timmons |
| 4,078,568 A | 3/1978 | Etes et al. |
| 4,140,115 A | 2/1979 | Schonfeld |

(Continued)

FOREIGN PATENT DOCUMENTS

| EP | 1023024 A1 | 8/2000 |
| EP | 0776645 B1 | 3/2002 |

(Continued)

OTHER PUBLICATIONS

PCT Search Report mailed May 9, 2006, 4 pages.

*Primary Examiner* — Susan Su
(74) *Attorney, Agent, or Firm* — Charles R. Matson

(57) ABSTRACT

An absorbent article including features facilitating toilet training of a wearer is provided. The article includes at least a first appearing graphic that changes from an initial, less visible state to a subsequent, more visible state in the absence of wetness, thereby to provide positive encouragement to a child during toilet training. The appearing graphic becomes less visible if subjected to liquid. A wetness sensation member may also be provided to give tactile, negative sensation to the child, thereby giving feedback received by at least two different senses. Additionally or alternatively, a second appearing graphic, different from the first appearing graphic, may be provided to increase a child's interest in the toilet training process. The first and second appearing graphics may become visible at different times, thereby providing a sequential or spaced reveal of the image.

8 Claims, 13 Drawing Sheets

(56) References Cited

U.S. PATENT DOCUMENTS

| | | |
|---|---|---|
| 4,192,311 A | 3/1980 | Felfoldi |
| 4,192,785 A | 3/1980 | Chen et al. |
| 4,231,369 A | 11/1980 | Sorensen et al. |
| 4,231,370 A | 11/1980 | Mroz |
| 4,292,916 A | 10/1981 | Bradley et al. |
| 4,327,731 A | 5/1982 | Powell |
| 4,393,080 A | 7/1983 | Pawelchak et al. |
| 4,505,976 A | 3/1985 | Doehnert et al. |
| 4,507,121 A | 3/1985 | Leung |
| 4,551,490 A | 11/1985 | Doyle et al. |
| 4,593,053 A | 6/1986 | Jevne et al. |
| 4,669,146 A | 6/1987 | Saito et al. |
| 4,705,513 A | 11/1987 | Sheldon |
| 4,738,257 A | 4/1988 | Meyer et al. |
| 4,768,503 A | 9/1988 | Highgate et al. |
| 4,892,536 A | 1/1990 | Desmarais et al. |
| 4,990,147 A | 2/1991 | Freeland |
| 5,037,416 A | 8/1991 | Allen et al. |
| 5,151,092 A | 9/1992 | Buell et al. |
| 5,197,958 A | 3/1993 | Howell |
| 5,269,775 A | 12/1993 | Freeland et al. |
| 5,468,236 A | 11/1995 | Everhart |
| 5,614,586 A | 3/1997 | Tang et al. |
| 5,674,275 A | 10/1997 | Tang et al. |
| 5,726,250 A | 3/1998 | Zajaczkowski |
| 5,766,212 A | 6/1998 | Jitoe |
| 6,075,178 A | 6/2000 | La Wilhelm |
| 6,284,942 B1 | 9/2001 | Rabin |
| 6,297,424 B1 | 10/2001 | Olson et al. |
| 6,307,119 B1 | 10/2001 | Cammarota |
| 6,428,526 B1 | 8/2002 | Heindel et al. |
| 6,482,191 B1 | 11/2002 | Roe et al. |
| 6,596,918 B1 | 7/2003 | Wehrle |
| 6,627,786 B2 | 9/2003 | Roe et al. |
| 6,635,797 B2 | 10/2003 | Olson et al. |
| 6,710,221 B1 | 3/2004 | Pierce |
| 6,719,742 B1 | 4/2004 | McCormack et al. |
| 6,726,668 B2 | 4/2004 | Underhill et al. |
| 6,772,708 B2 | 8/2004 | Klofta |
| 6,881,206 B2 | 4/2005 | Underhill et al. |
| 6,896,521 B2 | 5/2005 | Underhill et al. |
| 6,904,865 B2 | 6/2005 | Klofta et al. |
| 7,153,561 B2 | 12/2006 | Larson et al. |
| 7,280,441 B2 | 10/2007 | MacDonald et al. |
| 8,445,743 B2 * | 5/2013 | Roe et al. .................. 604/361 |
| 2003/0060794 A1 | 3/2003 | Olson |
| 2003/0073966 A1 | 4/2003 | Sosalla |
| 2003/0100872 A1 * | 5/2003 | Roe et al. .................. 604/361 |
| 2004/0064113 A1 | 4/2004 | Erdman |
| 2004/0127867 A1 | 7/2004 | Odorzynski et al. |
| 2004/0138633 A1 | 7/2004 | Mishima et al. |
| 2004/0191118 A1 | 9/2004 | Mody |
| 2004/0220540 A1 | 11/2004 | Underhill et al. |
| 2005/0049568 A1 | 3/2005 | Underhill et al. |
| 2005/0065489 A1 | 3/2005 | Driskell et al. |
| 2005/0096612 A1 | 5/2005 | Davis et al. |
| 2005/0124947 A1 | 6/2005 | Fernfors |
| 2005/0125877 A1 | 6/2005 | Benjamin et al. |
| 2005/0148961 A1 | 7/2005 | Sosalla et al. |
| 2006/0004333 A1 | 1/2006 | Olson |
| 2006/0114754 A1 | 6/2006 | MacDonald et al. |
| 2012/0323198 A1 * | 12/2012 | Pesce et al. .................. 604/367 |

FOREIGN PATENT DOCUMENTS

| | | |
|---|---|---|
| EP | 1216673 A1 | 6/2002 |
| EP | 1222907 A2 | 7/2002 |
| EP | 1356798 A1 | 10/2003 |
| JP | 2004 222868 A | 8/2004 |
| WO | WO 94/13235 A1 | 6/1994 |
| WO | WO 00/00233 A1 | 1/2000 |
| WO | WO 00/15169 A1 | 3/2000 |
| WO | WO 00/76442 A | 12/2000 |
| WO | WO 01/41691 A1 | 6/2001 |
| WO | WO 01/50996 A | 7/2001 |
| WO | WO 01/95845 A1 | 12/2001 |
| WO | WO 02/49564 A1 | 6/2002 |
| WO | WO 04/028403 A2 | 4/2004 |
| WO | WO 2005/048902 A | 6/2005 |

* cited by examiner

ABSORBENT ARTICLE HAVING DRYNESS INDICATING GRAPHIC

FIELD OF THE DISCLOSURE

The present disclosure is applicable to absorbent articles including diapers, training pants, pull-on diapers, incontinence briefs, incontinence undergarments, absorbent inserts, diaper holders and liners, and the like. This disclosure is particularly related to absorbent articles having dryness indicating graphics suited for urinary toilet training.

BACKGROUND OF THE DISCLOSURE

Absorbent articles are well known in the art. These articles typically have an absorbent assembly held or positioned in proximity to the body of a wearer during use in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. Disposable diapers typically comprise a single design available in different sizes to fit a variety of wearers ranging from newborns to toddlers undergoing toilet training. The design of the diaper typically affects performance, such as the ability to absorb and contain bodily waste. The fit of the diaper on the wearer's body is typically affected by, for example, the size of the diaper waist opening, the size of the openings around the thighs, and the length or "pitch" of the diaper.

The toilet training stage may be referred to as the "point of exit" from the diaper product category because toddlers who have successfully completed toilet training typically no longer wear diapers. The age at which children are toilet trained in "developed" countries has increased steadily over the past several decades and is now in the range of about 24-48 months. One reason for which toilet training has become delayed is that significant technical improvements have been made in diaper dryness and comfort. For example, when wearing a typical modern diaper, the child may have dry skin even after one or more occurrences of urination. As a result, the child may feel little or no discomfort and often may not even be aware that he or she has urinated. However, having the child feel discomfort following urination in his or her "pants" may assist with learning and/or provide motivation to learn to voluntarily retain urine. It is possible to use cloth training pants that leave the skin wet and, due to their high breathability, promote evaporative cooling of the skin, further enhancing discomfort. However, cloth training pants have poor urine containment, often leading to wet clothing and wet surroundings, e.g., carpeting, furniture, etc.

In addition to tactile feedback, the toilet training process may incorporate a wide variety of different aspects, including many training techniques and training aids that may be used by a caregiver. One aspect of the toilet training process is the change from diapers to training pants, during which the child is taught to use a toilet just like adults. Another aspect of the toilet training process includes caregiver instruction as a positive encouragement and reinforcement to the child that he or she should now be using a toilet instead of diapers.

Unfortunately, conventional training techniques often focus on providing negative feedback rather than positive encouragement to stay dry. Articles are known which have an "active" graphic that disappears in the presence of urine. Such graphics provide negative reinforcement to the child that he or she has wet the article, but do not provide encouragement during the period during which the article was dry. Accordingly, such disappearing graphics may have only limited effect.

The prior art also generally suggests the use of active graphics that appear over time, thereby to provide positive encouragement to the child. U.S. Pat. No. 6,635,797, which issued to Olson et al. on Oct. 21, 2003, discloses an "active" graphic that becomes more visible with the passage of time when exposed to the environment but not exposed to urine. Olson et al. teach that the "active" graphic is an object, such as a fish or a butterfly. The "active" graphic may also be a plurality of the same object, such as a plurality of fish or a plurality of butterflies. The use of repetitive "active" graphics, however, is potentially monotonous and therefore risks losing the child's interest in the toilet training process.

The prior art is limited to providing a single type of sensory feedback. Articles that facilitate transmission of temperature changes or wetness following urination provide a negative, tactile reminder to the child. "Active" graphics that disappear upon contact by urine provide a negative, visual reminder. Active graphics that appear over time provide a positive, visual reminder.

Thus, it would be desirable to provide an article that can facilitate urinary toilet training by providing different appearing graphics that captivate and maintain a child's interest. It would also be desirable for an article to provide multi-sensory feedback to a child that may send redundant or different reminders during the toilet training process.

SUMMARY OF THE DISCLOSURE

An absorbent article including features facilitating toilet training of a wearer is provided. The article includes a backsheet having an interior surface and an opposite exterior surface, and an absorbent assembly disposed on the interior surface. A first appearing graphic is disposed on one of the backsheet and absorbent assembly and viewable at the exterior surface. The first appearing graphic has an initial state in which the first appearing graphic is less visible and, after a first period of time, a subsequent state in which the first appearing graphic is more visible. A second appearing graphic, different from the first appearing graphic, is disposed on one of the back sheet and absorbent assembly and viewable at the exterior surface. The second appearing graphic has an initial state in which the second appearing graphic is less visible and, after a second period of time different from the first period of time, a subsequent state in which the second appearing graphic is more visible. The use of different graphics which appear at different time intervals is better able to attract and maintain a child's attention and focus during the toilet training process.

In addition, an absorbent article providing multi-sensory feedback to a child is provided. An absorbent article for wearing about a lower torso of a wearer and having a longitudinal axis has two laterally opposed article side edges extending between a laterally extending first waist end edge in a first waist region and a laterally extending second waist end edge in a second waist region, and a crotch region interposed therebetween. The disposable absorbent article includes a backsheet, a topsheet joined to the backsheet and having a body-facing surface, and an absorbent assembly disposed intermediate the backsheet and the topsheet. At least one wetness sensation member is positioned to closely contact a wearer's skin during use. The wetness sensation member includes a permeable layer and an impermeable layer disposed in face-to-face arrangement with the permeable layer, wherein urine deposited onto the wetness sensation member can penetrate through the permeable layer in a z direction to the impermeable layer and wherein the impermeable layer prevents urine from passing completely through the member in the z direction and supports movement of urine in an x-y plane such that the wearer's awareness of urination is enhanced. At least a first appearing graphic is disposed on one of the backsheet and absorbent assembly and viewable at the exterior surface. The first appearing graphic has an initial state in which the first appearing graphic is less visible and, after a first period of time, a subsequent state in which the first appearing graphic is more visible. Accordingly, the wetness sensation member provides tactile negative reinforcement while the appearing graphic provides positive visual encouragement to a child during the toilet training process.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

FIG. 5b is a cross sectional view of the disposable absorbent article illustrated in FIG. 5a.

FIG. 6b is a cross sectional view of the disposable absorbent article illustrated in FIG. 6a.

FIG. 7b is a cross sectional view of the disposable absorbent article illustrated in FIG. 7a.

FIG. 8b is a cross sectional view of the disposable absorbent article illustrated in FIG. 8a.

FIG. 9b is a cross sectional view of the disposable absorbent article illustrated in FIG. 9a.

In FIG. 10, the interior portion of the article 20 that faces inwardly toward the wearer and contacts the wearer is shown facing upward.

DETAILED DESCRIPTION OF THE DISCLOSURE

Definitions

Figure 1:
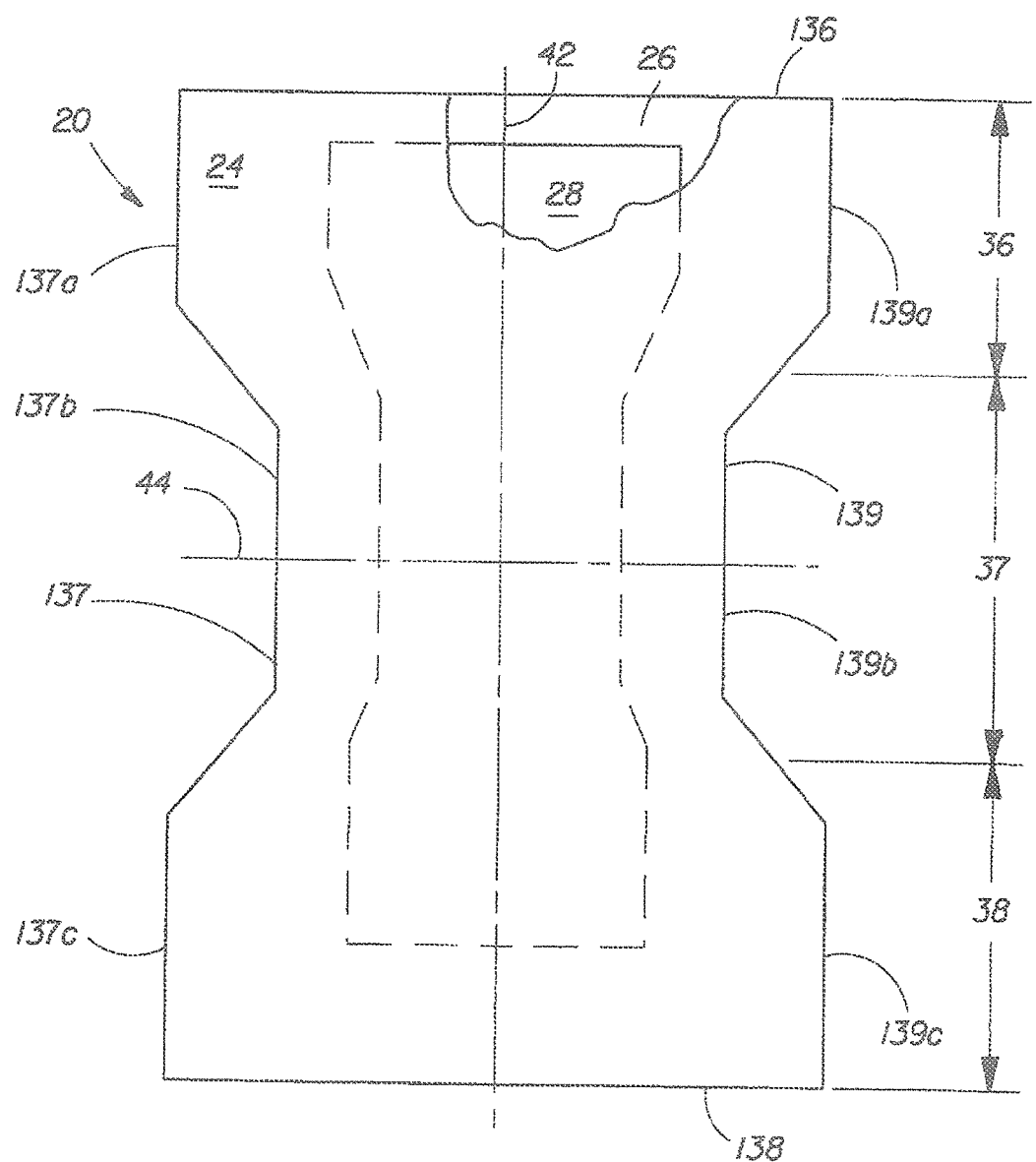
FIG. 1 is a plan view of a disposable absorbent article.

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "unitary" refers to an absorbent article that is formed of separate parts united together to form a coordinated entity so as to not require separate manipulative parts like a separate holder and liner.

The term "disposed" refers to an element being attached and positioned in a particular place or position in a unitary structure with other elements.

The term "diaper" refers to an absorbent article generally worn by infants and incontinent persons about the lower torso and having the general form of a sheet, different portions of which are fastened together to encircle the waist and the legs of the wearer.

The term "training pants" refers to an absorbent article generally worn by infants and incontinent persons about the lower torso and having the general form of a pair of short pants that can be applied or removed from the wearer without unfastening.

The term "refastenable" refers to the property of two elements being capable of releasable attachment, separation, and subsequent releasable reattachment without substantial permanent deformation or rupture.

The terms "releasably attached," "releasably engaged", and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

The term "toilet training" refers to the development of continence, which is the ability to voluntarily retain one's urine and feces. Individuals who are incontinent are unable to voluntarily retain their bodily discharges and, instead, urinate and defecate reflexively. For example, newborn babies are incontinent. Coincident with the development of continence, children typically develop the ability to voluntarily urinate and defecate, and cease reflexive elimination. This development of continence and of voluntary elimination, in place of reflexive elimination, may be accelerated and/or guided by caregivers through associative and conditioning techniques of training the child. For the purpose of the present disclosure, the term "toilet training" is used to denote training both for continence, itself, and for the voluntary elimination that is associated with continence. It is also noted that the term "toilet training" is synonymous with the term "potty training".

The term "longitudinal" refers to a direction running parallel to the maximum linear dimension of the article and includes directions within ±45° of the longitudinal direction.

The term "lateral" or "transverse" refers to a direction running at a 90 degree angle to the longitudinal direction and includes directions within ±45° of the lateral direction.

The term "x-y plane" refers to the generally planar structure of a sheet material defined by its length and width and lies between the sheet material's two major surfaces regardless of whether or not the sheet material is flat or curved.

The term "z-direction" refers to the direction through the thickness of a sheet material and generally orthogonal to the x-y plane.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The term "retard" refers to the hindrance or the prevention of the flow of liquid water. In the context of the term "flow control layer", both terms together refer to the fact that different layers in a layered structure may be water-permeable, yet differ in the respective flow rates at which they permit liquid water, and likewise bodily wastes that are aqueous in nature, to pass through their respective thicknesses. For example, a layer containing capillary channels and through whose thickness liquid water wicks in the absence of any forcing pressure is considered to be water-permeable. However, the flow rate at which liquid water can pass through the thickness of such a layer may be lower than the flow rate at which liquid water can pass through the thickness of a layer containing holes that are too large to act as capillary channels. Similarly, two layers both containing capillary channels and through whose thicknesses liquid water wicks in the absence of any forcing pressure are both considered to be water-permeable. However, the capillary channels in one of the layers may differ in size from those in the other layer or may be more numerous than those in the other layer, such that the wicking flow rate of liquid water through the one layer may be greater than that through the other layer. Thus, in a layered structure, one layer serving as a flow control layer may retard the passage of liquid water through the thickness of the layered structure, relative to the greater flow rate at which another of the layers would permit the passage of the liquid water through its thickness in the absence of the flow control layer. It is noted that when the flow control layer is water-impermeable, it effectively prevents the passage of liquid water through its thickness in the absence of a forcing pressure, i.e., the prevention of the passage of liquid water is included within the meaning of the term "retard".

The term "visible" refers to the quality of being capable of being seen by the naked eye under conditions of normal room lighting or in natural light during the daytime. Becoming "more visible" or "less visible" means changing in visibility to a noticeable extent when viewed under a generally constant or equal lighting condition.

The term "visible highlighting" refers to the visible differentiation of an object such that it noticeably stands out from its surroundings, e.g., by differing in coloration, hue, or tint, by differing in lightness, darkness, or contrast, by differing due to the presence or absence of graphical or solid color forms, or by any other variation serving to create noticeable visible differentiation.

The term "coloring" refers to the effect produced by applying or combining colors in and/or on an object or a portion of an object.

The term "coloration" refers to the arrangement or degree of coloring especially when used to visibly differentiate an object or a portion of an object in order to visibly highlight it.

The term "solid coloring" refers to the unbroken, i.e., uninterrupted, coloring of an area as contrasted with the discrete line-like form of some graphics.

The term "graphic" refers to a product of graphic art or a graphic representation in a pictorial form. A graphic may be a symbol, shape, image, text, or other form of indicia.

The term "associative correlation" refers to establishing a mutual or reciprocal relation between the visible highlighting and that with which it is being associatively correlated so that an association, i.e. a mental connection or bond, is formed between the two. This term is used in the context of associatively correlating the respective visible forms of the visible highlighting and an externally visible graphics in or on the absorbent article as well as in the context of associatively correlating the visible highlighting or graphics with the concept of urinary toilet training, For example, associatively correlated graphics may serve in concert to draw attention to an opportunity for urinary toilet training when an absorbent article is viewed prior to its being worn, to provide an externally visible reminder of the presence of the wetness sensation member in the interior of the absorbent article while it is being worn, etc. Similarly, visible highlighting that provides a visual reference to a topic related to urinary toilet training, such as dryness, wetness, or protection from wetness, may serve to associatively correlate the visible highlighting to the concept of urinary toilet training and thereby facilitate an opportunity for urinary toilet training.

The terms "interactively interrelated", "interactively unrelated", "related in subject matter", "unrelated in subject matter", and "related by a common story line" are intended to have the same meanings as in U.S. Pat. No. 6,297,424 issued to Olson et al. on 2 Oct. 2001, U.S. Pat. No. 6,635,797 issued to Olson, et al. on 21 Oct. 2003, and U.S. Pat. No. 6,307,119 issued to Cammarota et al. on 23 Oct. 2001.

FIG. 1 is a plan view of an exemplary disposable absorbent article 20 in its flat out, uncontracted state, i.e., without elastic-induced contraction, with portions of the structure being cut away to more clearly show the underlying structure of the disposable absorbent article 20 and with the portion of the disposable absorbent article 20 which contacts the wearer facing the viewer (i.e., showing the interior or inner side of the article). The disposable absorbent article 20 has a longitudinal axis 42 and a transverse axis 44. One end portion of the disposable absorbent article 20 is configured as a first waist region 36 of the disposable absorbent article 20. The opposite end portion is configured as a second waist region 38 of the disposable absorbent article 20. The waist regions 36 and 38 generally comprise those portions of the disposable absorbent article 20 which, when worn, encircle the waist of the wearer. The waist regions 36 and 38 may include elastic elements such that they gather about the waist of the wearer to provide improved fit and containment. An intermediate portion of the disposable absorbent article 20 is configured as a crotch region 37, which extends longitudinally between the first and second waist regions 36 and 38. The crotch region 37 is that portion of the disposable absorbent article 20 which, when the disposable absorbent article 20 is worn, is generally positioned between the legs of the wearer. The disposable absorbent article 20 has a laterally extending first waist edge 136 in the first waist region 36 and a longitudinally opposing and laterally extending second waist edge 138 in the second waist region 38. The disposable absorbent article 20 has a first side edge 137 and a laterally opposing second side edge 139, both side edges extending longitudinally between the first waist edge 136 and the second waist edge 138. The portion of the first side edge 137 in the first waist region 36 is designated 137a, the portion in the crotch region 37 is designated 137b, and the portion in the second waist region 38 is designated 137c. The corresponding portions of the second side edge 139 are designated 139a, 139b, and 139b, respectively.

The disposable absorbent article 20 preferably comprises a water-permeable topsheet 24, a water-impermeable backsheet 26, and an absorbent assembly 28 encased between the topsheet 24 and the backsheet 26. The topsheet 24 may be fully or partially elasticated or may be foreshortened so as to provide a void space between the topsheet 24 and the core 28 and/or to tend to draw the wetness sensation member 50 against the skin of the wearer. Exemplary structures including elasticized or foreshortened topsheets are described in more detail in U.S. Pat. No. 4,892,536 issued to DesMarais et al. on Jan. 9, 1990, U.S. Pat. No. 4,990,147 issued to Freeland on Feb. 5, 1991, U.S. Pat. No. 5,037,416 issued to Allen et al. on Aug. 6, 1991, and U.S. Pat. No. 5,269,775 issued to Freeland et al. on Dec. 14, 1993.

The disposable absorbent article 20 may include a variety of features known in the art, such as outer leg cuffs, barrier leg cuffs, front and rear ear panels, waist cap features, elastics, and the like to provide desired fit, containment, and aesthetic characteristics. Such additional features are well known in the art and are described in U.S. Pat. No. 3,860,003 and U.S. Pat. No. 5,151,092, among others.

The exemplary disposable absorbent article 20 includes refastenable side seams 40 that can be used to fasten the waist regions together at the sides to apply the article like a diaper and that can also be used to configure the article like a pair of pull-on training pants, as described in more detail below. Alternatively, the disposable absorbent article 20 may by sealed at the sides.

Figure 2:
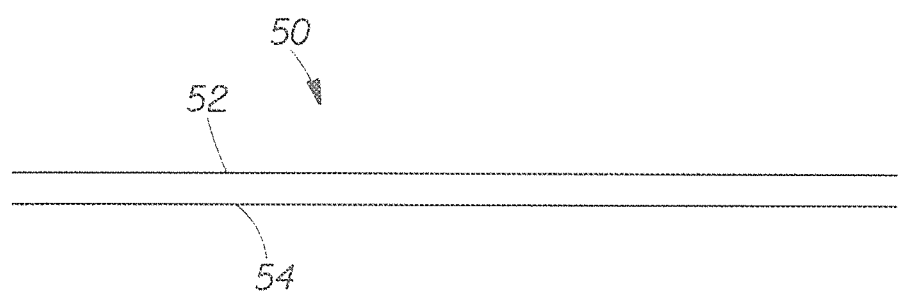
FIG. 2 is a cross sectional view of a wetness sensation member according to the present disclosure.

The disposable absorbent article 20 may include a wetness sensation member. Several suitable structures for a wetness sensation member are described in U.S. Pat. No. 6,627,786 issued on 30 Sep. 2003 in the name of Roe et al. An exemplary wetness sensation member is shown in FIG. 2. The wetness sensation member 50 comprises a water-permeable body-facing layer (upper layer) 52 and a flow control layer 54 disposed in a face-to-face arrangement with the water-permeable layer 52. The flow control layer is preferably impermeable to liquid water but permeable to vapor so that it is breathable. Preferably, but not necessarily, some portion of the wetness sensation member and/or a layer to which the wetness sensation member is attached is configured to draw the wetness sensation member toward the skin of the wearer, such as by being elastically foreshortened, formed to have a lesser length than another layer disposed relatively exteriorly, etc.

During insults of urine, the water-permeable layer allows urine to penetrate in the z-direction and also provides a medium for the flow of urine in the x-y plane via wicking. The flow control layer retards the passage of the urine through the wetness sensation member in the z-direction, thereby expanding the wetted area of the wetness sensation member, which preferably is held in contact with the wearer's skin. The combination of limited penetration in the z-direction and wicking in the x-y plane causes the urine to spread out and effectively wet a large area before being absorbed into the absorbent assembly, thereby maximizing the wetness signal experienced by the wearer.

Exemplary water-permeable layers suitable for use in the wetness sensation members include nonwovens, foams, woven materials, etc. The water-permeable layer is preferably hydrophilic. Exemplary flow control layers suitable for use in the wetness sensation members include polyolefinic films, microporous or breathable films, other films, and hydrophobic nonwovens. Suitable hydrophobic nonwovens include SM (spunbond meltblown), SMS (spunbond meltblown spunbond), and SMMS (spunbond meltblown meltblown spunbond) composites.

The disposable absorbent article 20 may include visible highlighting in the interior of the article to indicate the presence of the wetness sensation member or members and thereby facilitate an opportunity for the urinary toilet training of the wearer of the article. Such visible highlighting is described in co-pending and commonly assigned U.S. patent application Ser. No. 10/697,225 filed on 30 Oct. 2003 in the name of Davis et al. Although a wetness sensation member lacking this visible highlighting is fully functional in terms of providing a noticeable wetness signal to the wearer, the caregiver might overlook or forget the possibility of capitalizing on each opportunity for urinary toilet training if the body-facing portion of the absorbent article presents a generally uniform appearance, such as in absorbent articles that present a generally uniform white appearance on their body-facing surfaces.

Furthermore, once the caregiver decides to mention urinary toilet training to the wearer, the visible highlighting can serve to draw the wearer's interest or can be pointed out by the caregiver and incorporated into an explanation of the upcoming opportunity. Thus, the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the wetness sensation member.

Even a simple solid coloring form of visible highlighting can serve to facilitate an opportunity for urinary toilet training, especially when used with wearers possessing some recognition of colors or colored forms. In addition, visible highlighting in the form of a color or colors may facilitate the teaching of recognition of colors and differences between colors, and the associated learning may enhance the urinary toilet training process in turn.

Because the wetness sensation member is located in what may be generally termed the laterally central region of the absorbent article, visibly highlighting the wetness sensation member may provide additional benefits related to the learning achieved by the wearer. For example, a visibly highlighted wetness sensation member may provide a line of reference for the visual separation of the two leg openings, including their differentiation into right and left leg openings for the respective feet to be inserted into the corresponding leg openings. Similarly, a longitudinally oriented visible highlighting may serve as a visual reference for the front to back direction, both for orienting the article prior to applying it, if done by the caregiver, or prior to donning it, if done by the wearer. This longitudinally oriented visual reference may also aid in the teaching of such skills as wiping one's self clean after using the toilet by using a longitudinal motion. The concept of something being central or "in the middle" may be taught and learned by visual reference to the visible highlighting and this concept may then be applied to related subjects, such as the anatomical location of the source of urine and the corresponding proper position in which to sit on the toilet. Thus, in the above and similar ways, the wearer can be made more aware of his or her own body, which may tend to enhance and facilitate the urinary toilet training experience.

In addition, the visible highlighting can serve to enhance the self-esteem of the wearer through a reminder that he or she is mature enough to be engaged in urinary toilet training. This effect can be compounded when the wearer succeeds in recognizing the need to go to the toilet and then sees the dry condition of the visibly highlighted wetness sensation member inside the article after pulling it down.

The visible highlighting may be provided by means of printing onto a surface of the wetness sensation member or one of its layers. For example, solid coloring or a graphic may be printed onto a surface of the flow control layer underlying the water-permeable layer. As another example, an adhesive or a gel may be printed onto a surface of either of the two layers. Such an adhesive or gel may be colored differently from the surrounding area. Alternatively, the adhesive or gel may be uncolored or may have the same color as the surrounding area, but may still provide visible highlighting by forming a distinctive raised area or pattern and/or by surrounding a distinctive recessed area or pattern.

The visible highlighting may also be provided by forming one or more layers of the wetness sensation member of a colored material, for example, a fibrous layer containing colored fibers, a monolithic layer containing a dispersed or imbedded colorant, a layer of an unbleached material that is colored in its virgin state, and so on.

In some embodiments, the visible highlighting may be provided by impressing or embossing the wetness sensation member or one of it layers. The impressed, embossed, or bonded portions of the wetness sensation member may provide a tactile sensation in addition to visibly highlighting the presence and location of the wetness sensation member. For instance, a raised area or a recessed area or the combination of raised and recessed areas adjacent to each other may be felt by the hand and, in some embodiments, may be felt by the wearer while wearing the article. Similarly, the raised area or pattern formed by a printed adhesive or gel, as mentioned above, may provide such a tactile sensation. Just as with the visible highlighting alone, the combination of visible highlighting and this tactile sensation can serve to draw the wearer's interest or can be pointed out by the caregiver and incorporated into an explanation of the upcoming opportunity for urinary toilet training.

In addition, the visible highlighting may be provided by incorporating distinctive fibers or filaments in one or both layers of the wetness sensation member or by distinctively orienting fibers or filaments in one of these layers. For example, a fiber or a filament of a distinctive color may be incorporated into the flow control material to visibly highlight its presence and its location in the article. Similarly, a distinctively thicker fiber or filament may be embedded in one of the two layers and thereby form a distinctive raised area or pattern.

If the portions of the structure of the absorbent article surrounding the wetness sensation member are of one color, the visible highlighting can be provided by the use of another color, by the use of contrast, by the use of a different pattern in the same or a similar color, or by any other method that visibly differentiates the wetness sensation member from the surrounding structural elements.

In some embodiments, the visible highlighting may include more than one color, more than one difference in contrast, more than one pattern, more than one graphic, more than one area of solid coloring, and so on, such that all portions of this description referring to the singular of a form of visible highlighting are meant to include the plural, and vice versa.

The visible highlighting may include open or closed geometric figures, a two dimensional representation of a three dimensional object, a representation of a commonly named or nameable shape or object, a representation of a recognizable object used in play, and/or a representation of a character that may be known to the wearer, such as a teddy bear, a character appearing on a television show for children, a character appearing in a game or a storybook for children, etc. In embodiments in which the visible highlighting includes a variety of figures, objects, and/or characters, the various elements of the visible highlighting may be interactively interrelated, related by subject matter, and/or related by a common story line. Conversely, the various elements may be interactively unrelated, unrelated by subject matter, and/or not related by a common story line.

When solid coloring is used, it may partially or completely fill the area bounded by a graphic outline, appear as shading inside or outside such a graphic outline, itself form a "filled-in" graphic, or simply uninterruptedly occupy an area, e.g., occupy the entire width of a layer of the wetness sensation member over all or a portion of the corresponding length.

In some embodiments, the visible highlighting may become more or less visible when the wetness sensation member is wetted. In addition, the visible highlighting may change color when the wetness sensation member is wetted. Any of these effects may be created by the use of inks or dyes or other agents that undergo chemical reactions or are dispersed or concentrated when wetted by urine. In general, any of the wetness indicating compositions commonly used in externally visible wetness indicators, such as so-called "appearing" or "disappearing" wetness indicators that may become more or less visible when wetted and in wetness indicators that may change color when wetted, may be used for these versions of visible highlighting.

It is important to note that rather than being structurally disposed in such a way as to provide a wetness indication that is visible from the outside of the absorbent article, any wetness indicating compositions used for the visible highlighting of the wetness sensation member must be visible from the body-facing surface of the absorbent article. This different disposition enables the caregiver to apply different techniques to the task of urinary toilet training when using an absorbent article of the present disclosure, as compared to using an absorbent article having only a wetness indicator visible from the outside of the article. For example, while the change in an exterior wetness indicator is visible for all to see, any change in the visible highlighting of an interior wetness sensation member remains "private" until either the caregiver or the wearer peers into the absorbent article or it is removed. Therefore, whether or not any wetting of the absorbent article has occurred can, itself, become the focus of a playful activity resembling a game, with the "secret" being revealed only when the caregiver and the wearer agree to conclude the game. If the wearer notices a sensation of wetness or merely desires to check the condition of the "private" indication, he or she can simply look inside the absorbent article. If the appearance of the visible highlighting has changed, the wearer can then choose to bring this to the attention of the caregiver in the context of asking to go to the bathroom. In addition, because the visible highlighting serves as a "private" indication, the wearer might be able to detect a change in its appearance before the appearance of any externally visible wetness indicator changes and thereby be the first person to mention the subject of going to the toilet. Furthermore, the provision of both visual and tactile sensations to the wearer may serve to reinforce the tactile sensation of wetness and thereby enhance the training effect of the wetness sensation member. An absorbent article in which the wetting is indicated by both a wetness sensation and a visible change in the appearance of the visible highlighting may thus facilitate faster learning on the part of the wearer.

Although the appearance of the visible highlighting remains "private" until either the caregiver or the wearer peers into the absorbent article or it is removed, the visible highlighting may be associatively correlated in visible form with marking that is located elsewhere in or on the absorbent article and is visible from the outside of the absorbent article. This externally visible marking may be permanent or may change in appearance while the absorbent article is being worn. For example, the externally visible marking may be an externally visible wetness indicator. By giving the visible highlighting of the wetness sensation member a visible form that is similar to the visible form of an externally visible marking, an opportunity for urinary toilet training may be enhanced. For instance, the caregiver can point out the similarity between the externally visible marking and the "private" visible highlighting of the wetness sensation member and ask the wearer to remember the hidden visible highlighting every time he or she notices the externally visible marking.

Even in embodiments in which the appearance of the visible highlighting is not affected by its being wetted, the associative correlation of the respective visible forms of an externally visible marking and the visible highlighting may serve to facilitate an opportunity for urinary toilet training. For example, if both the externally visible marking and the visible highlighting have the visible form of similar graphics, the externally visible marking can serve to draw the wearer's interest or can be pointed out by the caregiver and incorporated into an explanation of the ongoing opportunity for urinary toilet training.

Such associative correlation of the respective visible forms of an externally visible marking and the visible highlighting can be achieved without the respective visible forms being similar, so long as the respective visible forms are mutually related in a recognizable way. For example, the visible forms may be related in subject matter and/or may be related by a common story line and/or be interactively interrelated. Even an associative correlation of a simple solid coloring form of an externally visible marking with a similar solid coloring form of visible highlighting can serve to facilitate an opportunity for urinary toilet training, especially when used with wearers possessing some recognition of colors or colored forms.

Alternatively, the visible highlighting may be associatively uncorrelated with any externally visible marking. The lack of associative correlation may be complete or may be specific, e.g., the respective visible forms of the visible highlighting and the externally visible marking may be unrelated in subject matter, not related by a common story line, and/or interactively unrelated, while still being associatively correlated in another way.

The visible form of the visible highlighting of the wetness sensation member need not be associatively correlated with the concept of urinary toilet training. However, in some embodiments, the visible form of the visible highlighting may be associatively correlated with the concept of urinary toilet training by, for example, providing a visual reference to the liquid-related nature of urinary toilet training, such as wetness, dryness, protection from wetness, the flow of a liquid, water, et cetera, and thus may serve to facilitate an opportunity for urinary toilet training.

The visible highlighting may emphasize dryness by depicting the sun, fair weather clouds, a sunny day, etc., while wetness may be referenced by a depiction of a water puddle, a cloud with falling rain, etc. A visual reference to protection from wetness may be provided by a depiction of an umbrella, a raincoat, a rain hat, galoshes, a submarine, or some other object that may be associated by the wearer with the concept of staying dry in a wet environment.

In any of these visible forms of visible highlighting that are associatively correlated with the concept of urinary toilet training, a human form and/or a recognizable character may be depicted in the visible highlighting. For example, a child may be shown in conjunction with inanimate objects, a child may be shown sitting on a potty chair, and/or a character from a children's storybook or a children's television program may be shown in similar poses, etc.

The wetness sensation member according to the present disclosure may be arranged in an absorbent article in a variety of configurations. In addition, absorbent articles may include a single wetness sensation member or a plurality of wetness sensation members. In any event, the wetness sensation member(s) are preferably a part of, or attached to, an element or web, such as a topsheet, which is reliably held against the skin of the wearer. The wetness sensation member may extend over a portion of the disposable absorbent article spanning less than one half of the length of the article or else extend over a substantial part of the article spanning more than one half the length of the article. In addition, the wetness sensation member(s) are preferably positioned within the absorbent article to enhance the likelihood of being wetted with urine.

The wetness sensation member may also be releasably attached to or releasably engaged with the remainder of the absorbent article. In such a configuration, the wetness sensation member may be optionally removed from the absorbent article if the wetness sensation functionality is not desired. Such releasable attachment may be accomplished by a variety of known attachment means including adhesives, cohesives, ultrasonic bonding, thermal bonding, mechanical fasteners, or the like.

Figure 3A:
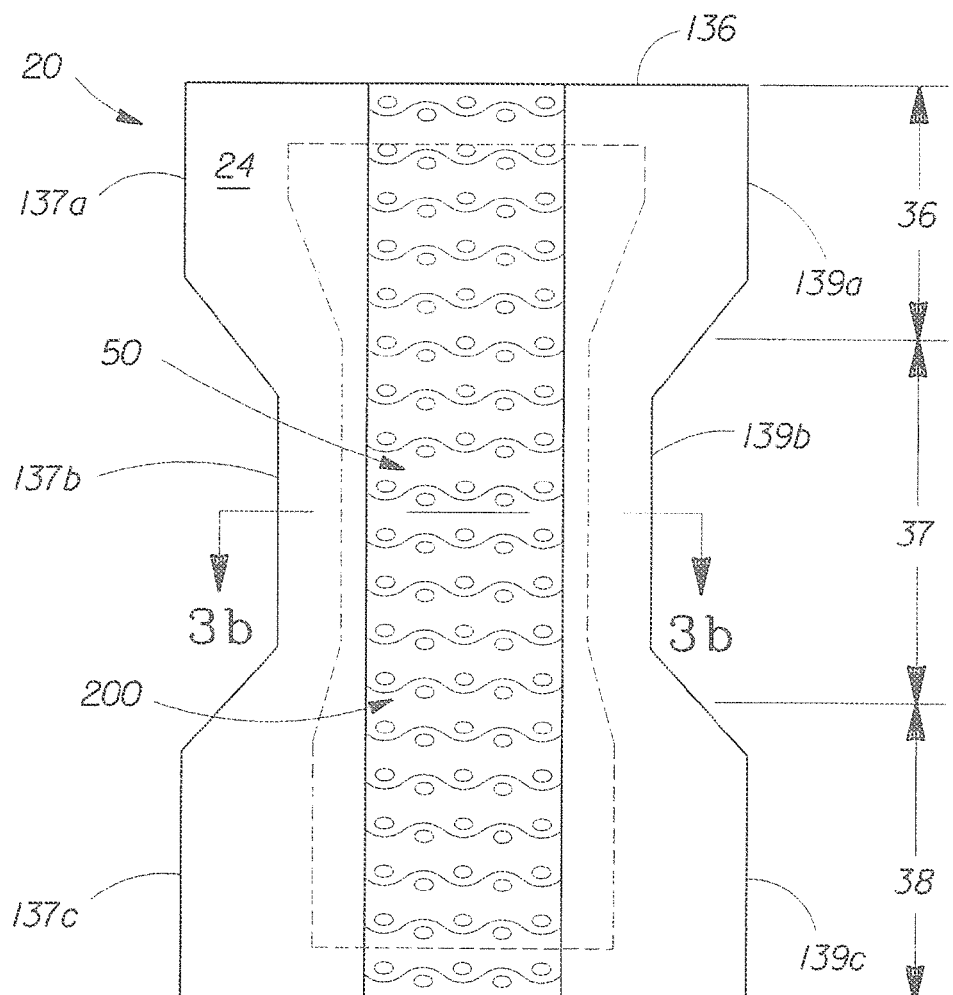
FIG. 3a is a plan view of a disposable absorbent article having a wetness sensation member disposed on a body-facing surface.
Figure 3B:
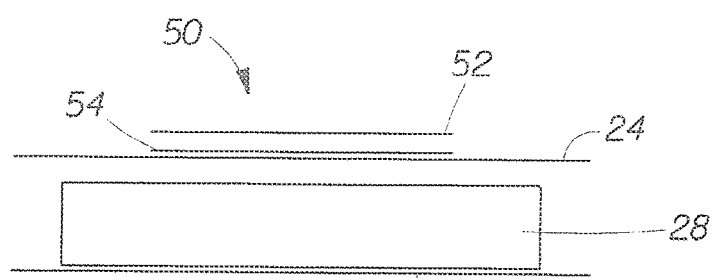
FIG. 3b is a cross sectional view of the disposable absorbent article shown in FIG. 3a illustrating the layers of the wetness sensation member.

An exemplary embodiment of a disposable absorbent article 20 including a wetness sensation member 50 disposed with the topsheet 24 is illustrated in FIG. 3*a* and FIG. 3*b*. The wetness sensation member in this embodiment is a separate composite member attached to the topsheet. The wetness sensation member comprises a water-permeable body-facing layer 52 and a flow control layer 54 disposed in a face-to-face arrangement with the body-facing layer. The visible highlighting 200 is shown in FIG. 3*a* as an exemplary pattern of wavy lines and circles.

Figure 4:
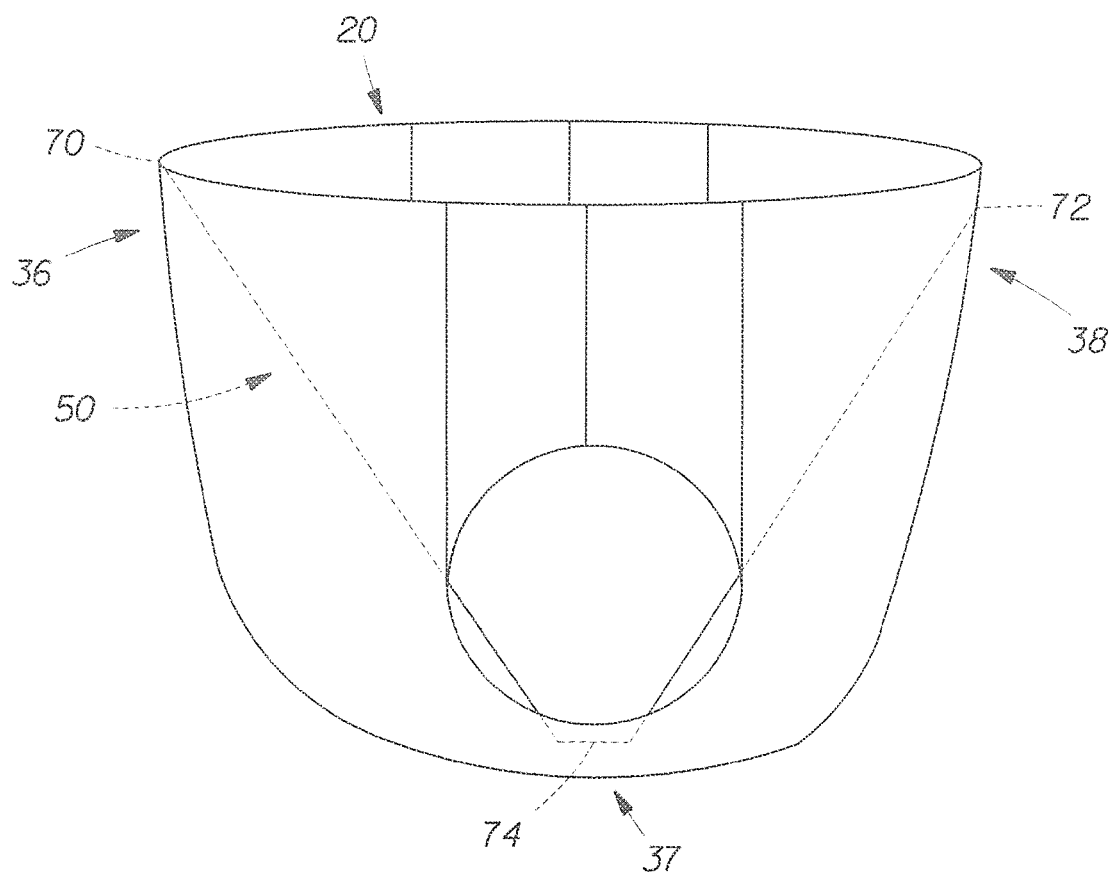
FIG. 4 is an isometric view of a pull-on disposable absorbent article illustrating the attachment of the wetness sensation member.

In an embodiment illustrated in FIG. 4, the wetness sensation member 50 has elastic properties and includes a first longitudinal end 70 attached to the first waist region 36 and a second longitudinal end 72 attached to the second waist region 38. In addition, a center portion 74 of the member 50 is preferably attached to the crotch region 37 in order to stabilize the member and facilitate fitting the article to the wearer, prevent interference with bowel movements and ensure good contact with the wearer's skin.

Figure 5A:
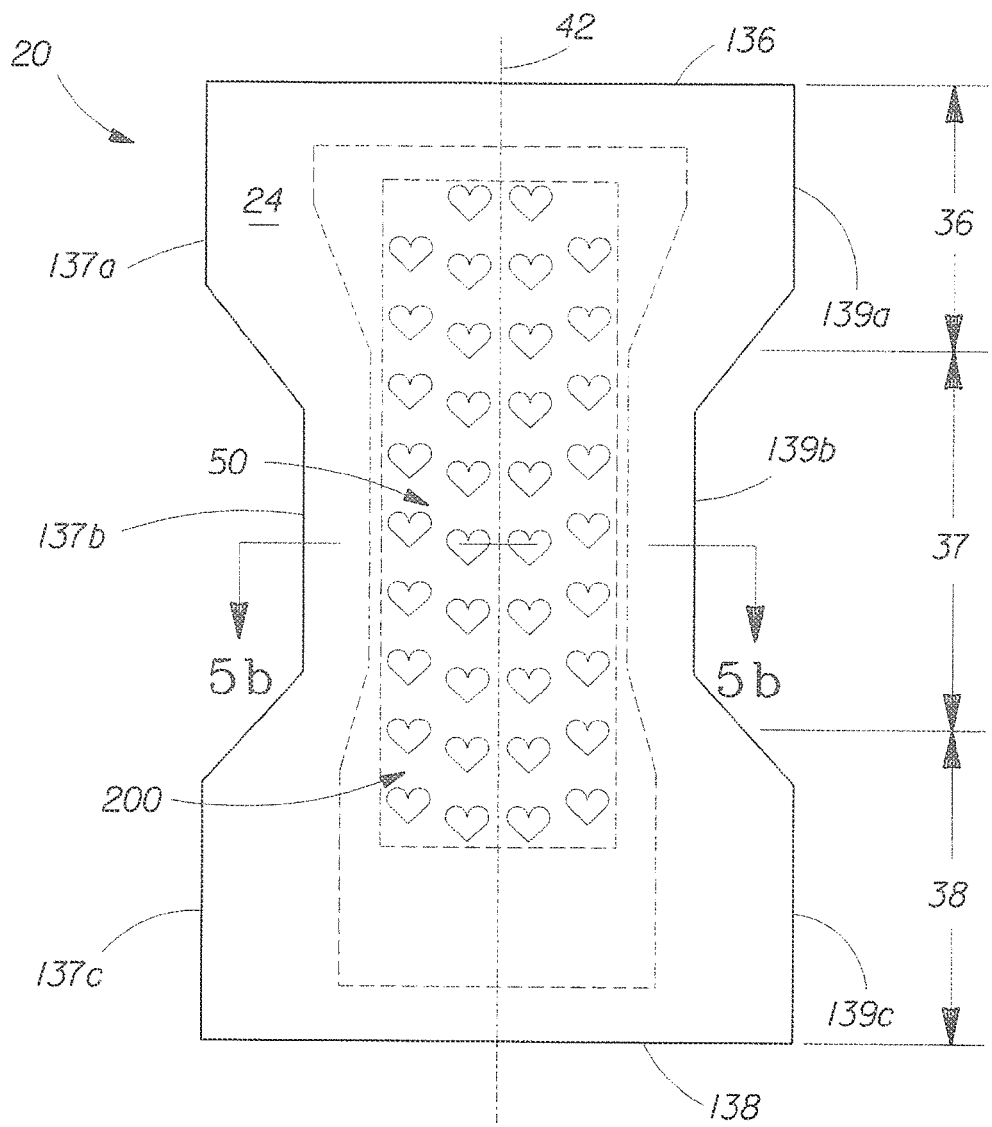
FIG. 5a is a plan view of a disposable absorbent article having a wetness sensation member integrated with the topsheet.
Figure 5B:
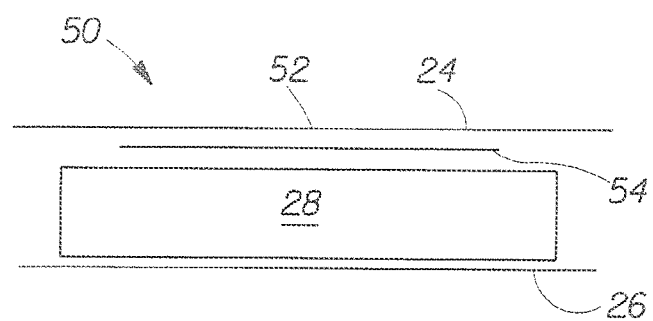

In an alternate embodiment shown in FIG. 5*a* and FIG. 5*b*, the flow control layer 54 of the wetness sensation member 50 is attached to the inner surface of the topsheet 24 such that a portion of the topsheet 24 serves as the water-permeable layer 52 of the wetness sensation member 50. For this embodiment, the topsheet 24 is preferably elastically foreshortened to deflect the wetness sensation member 50 into contact with the wearer's skin. Alternatively, this embodiment may include a topsheet that is shorter in length than the backsheet, having the longitudinal ends of the topsheet contiguous with the longitudinal ends of the backsheet so that as the disposable absorbent article is fitted around the wearer, the topsheet is forced into contact with the wearer's skin. The visible highlighting 200 is shown in FIG. 5*a* as an exemplary pattern of heart shapes.

Figure 6A:
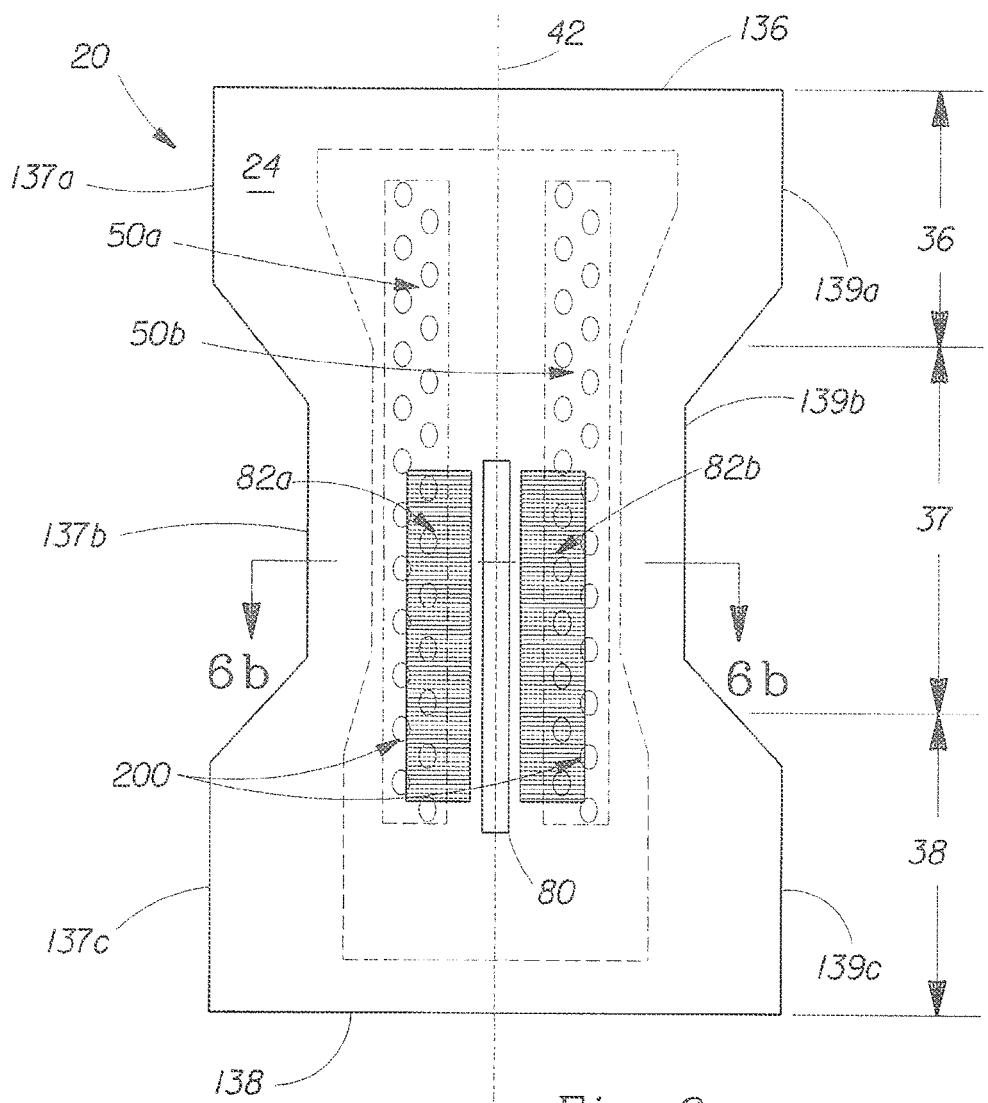
FIG. 6a is a plan view of a disposable absorbent article having two wetness sensation members integrated with the topsheet and disposed parallel to and spaced apart from the longitudinal axis with an elongated slit opening interposed therebetween.
Figure 6B:
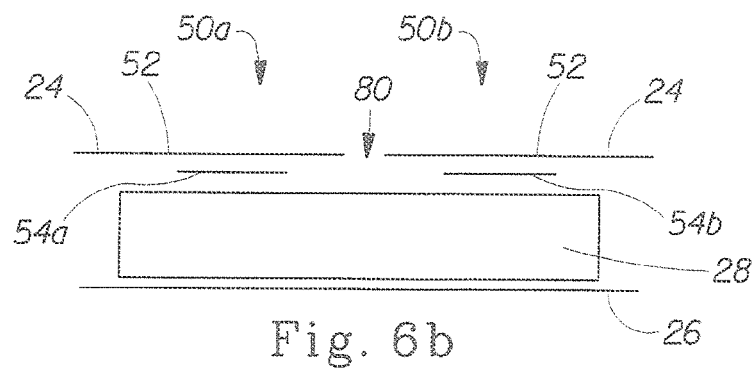

Absorbent articles according to the present disclosure may include a plurality of wetness sensation members disposed on the body-facing surface of the article. An example of an embodiment providing a plurality of wetness sensation members is shown in FIG. 6*a* and FIG. 6*b*. Two flow control layers 54*a* and 54*b* are attached to the bottom surface of the topsheet 24 forming two wetness sensation members 50*a* and 50*b*. For this embodiment, the flow control layers 54*a* and 54*b* are disposed between the topsheet and the absorbent assembly 28 so that the topsheet serves as the water-permeable layers 52 of the wetness sensation members. The two flow control layers 54*a* and 54*b* are disposed parallel to and spaced apart from the longitudinal centerline 42 of the disposable absorbent article 20. The spacing is determined to allow enough liquid to pass through to the core so as to prevent flooding that can result in leakage of the absorbent article during urination, while at the same time allowing enough liquid to flow and wick toward the flow control layers forming the wetness sensation members. The spacing between the flow control layers can be about 10 mm but can range from about 5 mm to about 15 mm and from about 8 mm and to about 12 mm. Although the embodiment shown in FIG. 6*a* and FIG. 6*b* has only two wetness sensation members, other absorbent article embodiments having three or more wetness sensation members are contemplated. The visible highlighting 200 is shown in FIG. 6*a* as an exemplary pattern of oblong ovaloid shapes.

As shown in FIG. 6*a* and FIG. 6*b*, the spacing of the flow control layers provides room for an elongated slit opening 80 in the topsheet 24. The elongated slit opening 80 is adapted to receive feces from the wearer and isolate the same from the wearer's skin. The elasticized regions 82*a* and 82*b* located adjacent to the slit opening 80 maintain alignment of the slit opening with the wearer's anus during use. The elasticized regions may also deflect the wetness sensation members toward the wearer's skin to maintain contact therewith during use. Exemplary elasticized topsheets including elongated slit openings are disclosed in U.S. Pat. No. 6,482,191 issued 19 Nov. 2002 in the name of Roe et al. Alternatively, the flow control layers 54*a* and 54*b* of the wetness sensation members may be elastically foreshortened to provide benefits similar to those provided by the elasticized regions disposed in the topsheet.

Figure 7A:
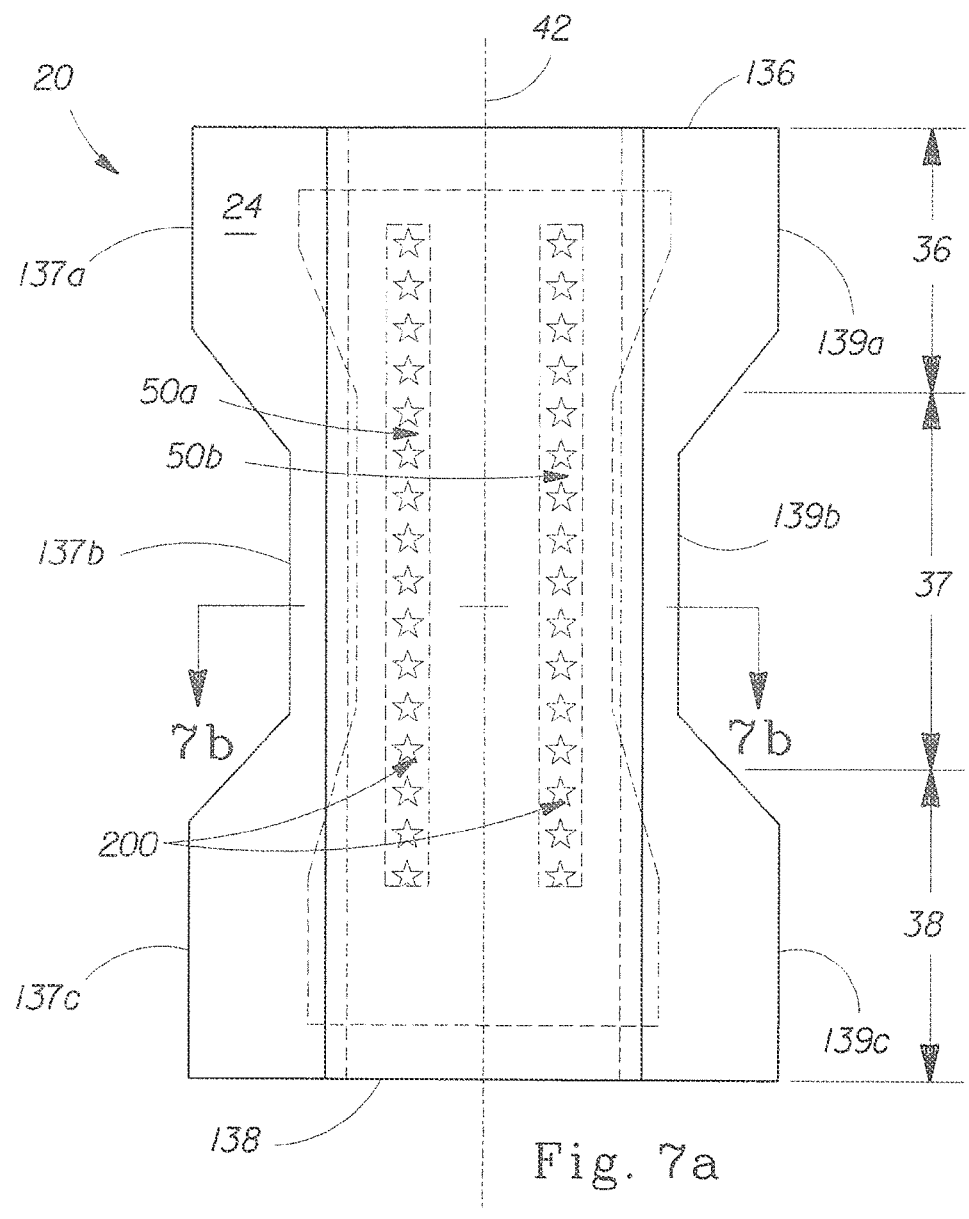
FIG. 7a is a plan view of a disposable absorbent article having a Z-folded topsheet with two wetness sensation members integrated with the topsheet and disposed in the Z-folds in the topsheet.
Figure 7B:
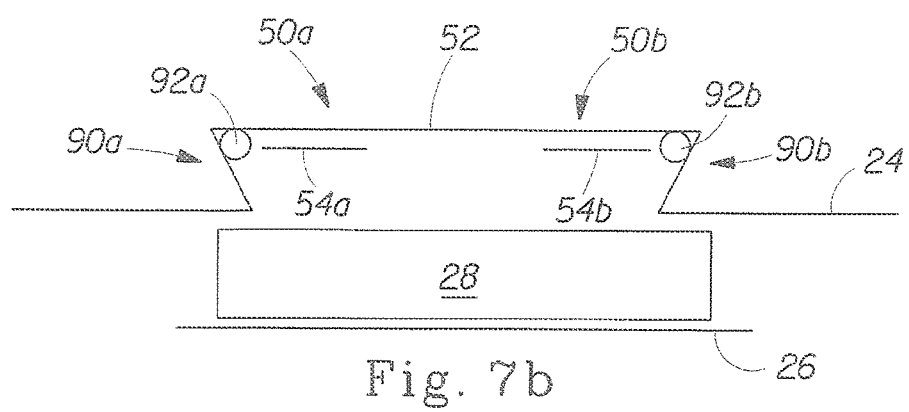

In another alternate embodiment shown in FIG. 7*a* and FIG. 7*b*, the topsheet 24 serves as the water-permeable layer 52 similar to the previous embodiment. However, the flow control layers 54*a* and 54*b* are disposed in two parallel oppositely facing Z-folds 90*a* and 90*b* formed in the topsheet 24 along the longitudinal length of the disposable absorbent article 20, thus forming two wetness sensation members 50*a* and 50*b*. The Z-folded topsheet may be attached to the underlying layers along the longitudinal edges of the topsheet 24, thus allowing the portion of the topsheet between the Z-folds to float freely. Longitudinally extending elastic elements 92*a* and 92*b* are disposed along the flow control layers 54*a* and 54*b* in order to deflect the center portion of the Z-folded topsheet away from the absorbent assembly 28. The elastic elements may be disposed along the outer edges of the flow control layers 54a and 54b as shown in FIG. 7b, or alternatively, may be disposed in a face-to-face arrangement with the flow control layers. The combination of the Z-folded topsheet and the elastic elements maintains the wetness sensation members in contact with the wearer's skin in the event that the disposable absorbent article sags or fits loosely around the wearer. The visible highlighting 200 is shown in FIG. 7a as an exemplary pattern of star shapes.

In order to prevent the portion of the topsheet between the Z-folds from being forced into the gluteal groove and from interfering with the barrier leg cuffs, which are not shown in FIG. 7a or FIG. 7b, the spacing between the Z-folds can be about 65 mm and can range from about 50 mm to about 90 mm. Further, in order to control the deflection of the portion of the topsheet between the Z-folds, transverse bonds may be formed between the Z-folds in the first waist region, the second waist region and the crotch region using adhesives, ultrasonic bonds, radio frequency bonds, or other suitable means in order to control deflection. These transverse bonds may attach the Z-folded section to the body-facing surface of the topsheet and the section between the Z-folds to the underlying core.

As an alternative to a portion of the topsheet serving as a layer of a wetness sensation member, other components of the disposable absorbent article such as the barrier leg cuffs may serve as such a layer. The barrier leg cuffs may be made from either water-permeable or water-impermeable material. In either case, the barrier leg cuff material may serve as one of the layers of the wetness sensation member. In such exemplary embodiments, the structure of the barrier leg cuffs preferably holds the wetness sensation members in contact with the skin of the wearer to provide the sensation of wetness against the wearer's legs and/or crotch crease.

Figure 8A:
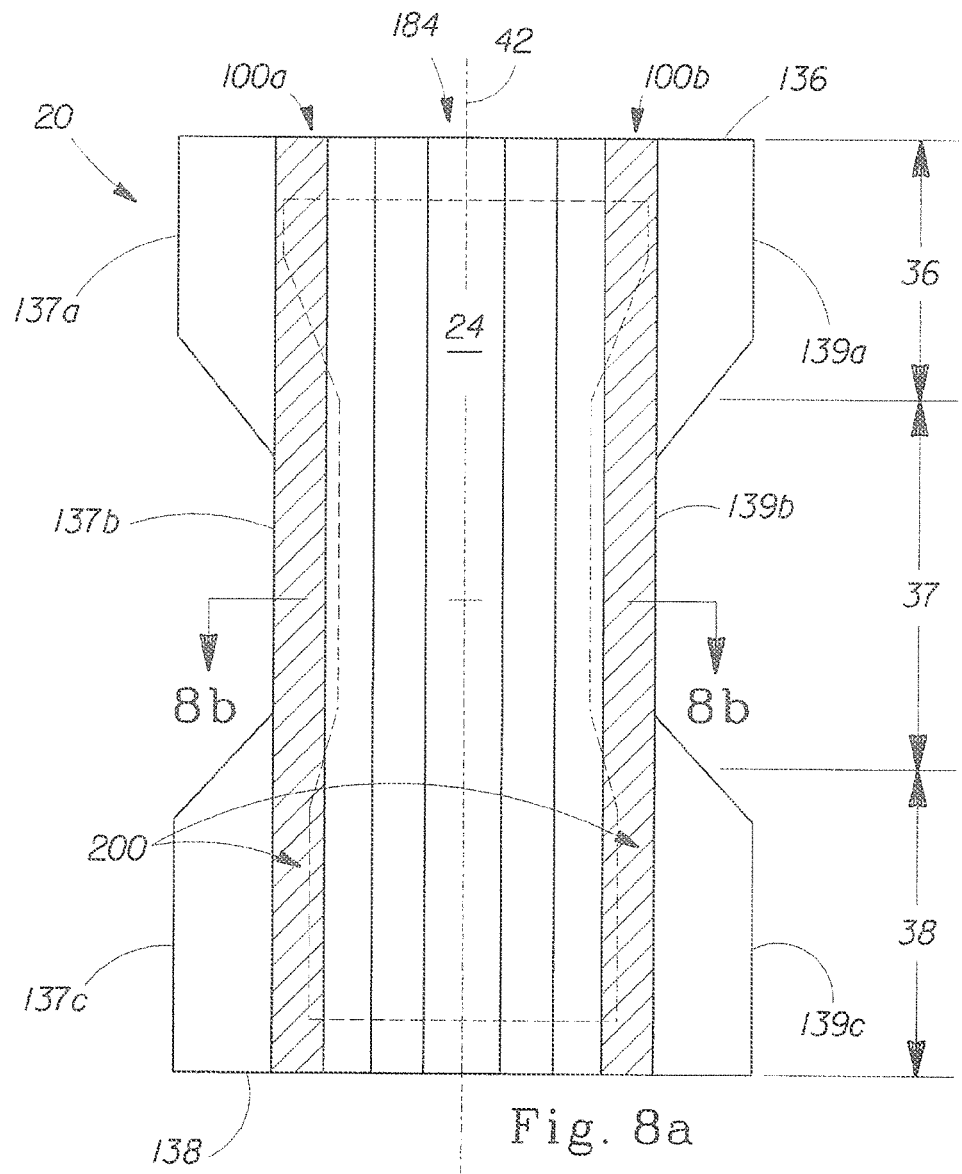
FIG. 8a is a plan view of a disposable absorbent article with barrier leg cuffs including wetness sensation members integrated with the barrier leg cuffs.
Figure 8B:
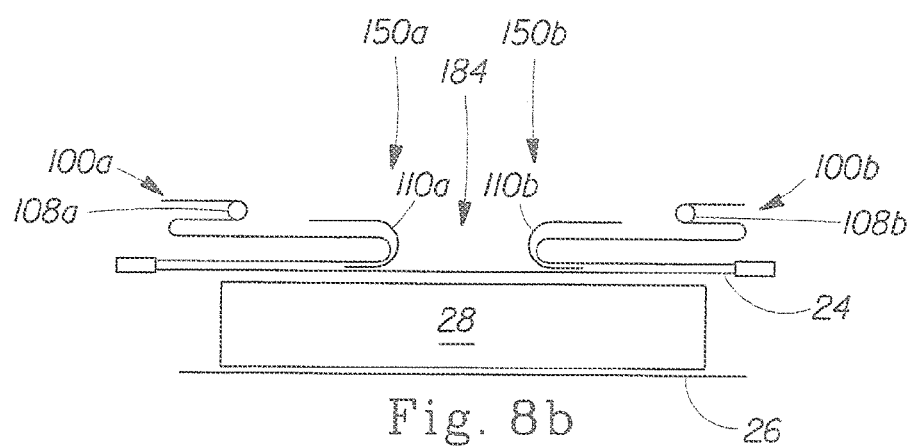

An exemplary embodiment in which barrier leg cuffs serve as layers of the wetness sensation members is shown in FIG. 8a and FIG. 8b. The disposable absorbent article 20 for this embodiment includes barrier leg cuffs 100a and 100b made from water-impermeable material and a portion of each barrier leg cuff serves as the flow control layer of the respective wetness sensation member. The water-permeable layer 110 can extend the length of each of the barrier leg cuffs and preferably extends at least the length of the crotch region 37 and the front waist region 36. The water-permeable layer 110 is preferably disposed on portions of the cuff closest to the longitudinal axis 42 of the disposable absorbent article 20 to increase the likelihood of becoming wetted during urination. As shown in FIG. 8a and FIG. 8b, the barrier leg cuffs 100a and 100b include elastic elements 108a and 108b, which serve to deflect the leg cuffs away from the topsheet 24 toward the skin of the wearer. The visible highlighting 200 is shown in FIG. 8a as an exemplary pattern of angled lines.

Figure 9A:
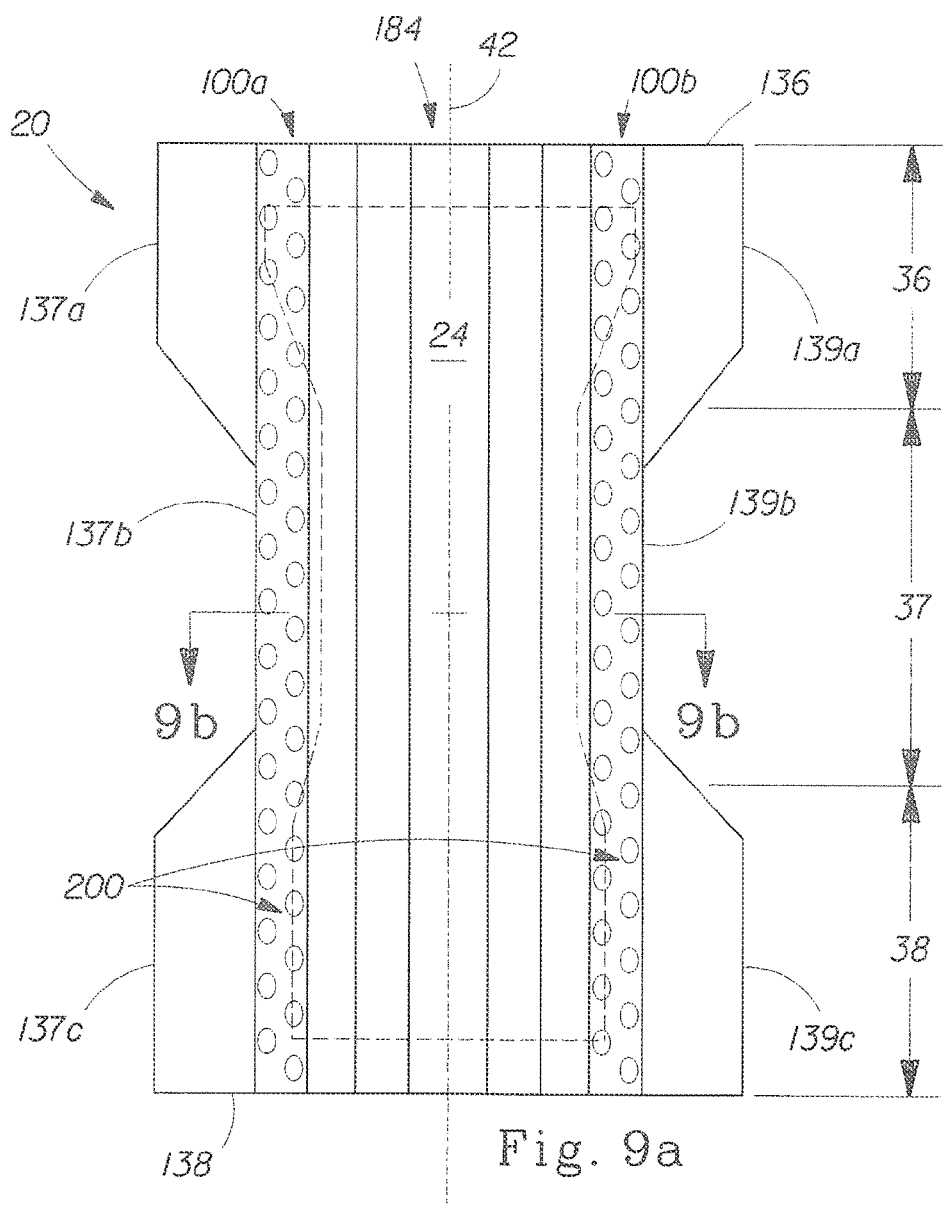
FIG. 9a is a plan view of a disposable absorbent article with an alternative form of barrier leg cuffs including wetness sensation members integrated with the barrier leg cuffs.
Figure 9B:
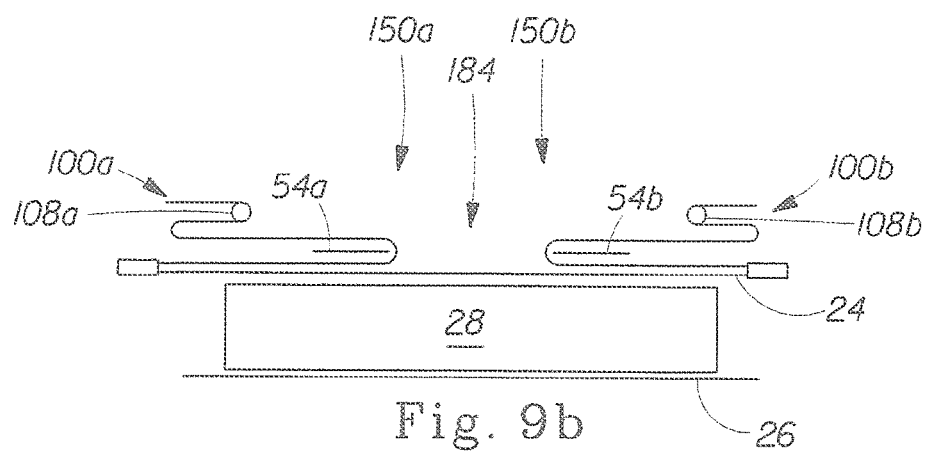

Another exemplary embodiment in which barrier leg cuffs serve as layers of the wetness sensation members is shown in FIG. 9a and FIG. 9b. In this embodiment, the barrier leg cuffs 100a and 100b are made of a water-permeable material and are otherwise arranged similarly to the embodiment shown in FIG. 8a and FIG. 8b. However, because the barrier leg cuff material serves as the water-permeable body-facing layer of each of the wetness sensations members 150a and 150b in this embodiment, flow control layers 54a and 54b are located between the absorbent assembly and each respective water-permeable layer formed by the barrier leg cuff material. The visible highlighting 200 is shown in FIG. 9a as an exemplary pattern of oval shapes.

The embodiments of wetness sensation members disclosed hereunder perform most effectively when held in contact with the skin of the wearer. In order to ensure that contact is made with the wearer's skin during use, the body-facing portion of the wetness sensation members may include a body-adhering composition, such as a topical adhesive, which acts to hold the wetness sensation member in place during use. The body-adhering composition may be applied to at least a portion of the body-facing surface of the wetness sensation member. However, the body-adhering composition may also be integral with the material making up the body-facing layer of the wetness sensation member. Further, the body-adhering composition may be disposed on any portion of the wetness sensation member contacting the skin of the wearer in any pattern or configuration including, but not limited to lines, stripes, dots, and the like. Such a body-adhering composition may include any of one or more substances capable of releasable adhering to the skin of the wearer, such as those disclosed in U.S. Pat. Nos. 4,231,369, 4,593,053, 4,699,146, 4,738,257, 5,726,250, 4,078,568, 4,140,115, 4,192,785, 4,393,080, 4,505,976, 4,551,490, 4,768,503, 5,614,586, and 5,674,275, and in the PCT Application published as WO 94/13235A1.

As previously mentioned, the exemplary disposable absorbent article 20 includes refastenable side seams that can be used to fasten the waist regions together at the sides to apply the article like a diaper onto the body of the wearer and that can also be used to configure the article like a pair of pull-on training pants. The refastenable side seams can be fastened by the user before the article is applied onto the body of the wearer and the article can then be applied like a pair of pull-on training pants. The refastenable side seams can be opened and refastened after the article is applied onto the body of the wearer in order to gain access for the inspection of the interior of the article and/or to adjust its fit while being worn. Of course, the side seams can also be opened for the ultimate removal of the article for disposal, as an alternative to leaving the article in the form of a pair of training pants and pulling it downward over the legs and feet for removal. The refastenable side seams also facilitate the pre-configuration of the article in the form of a pair of training pants prior to the point of sale to the consumer, if such a pre-fastened presentation is desired by the manufacturer, distributor, and/or retailer, while still providing the user with the alternative of opening the side seams in preparation for applying the article like a diaper.

Figure 10:
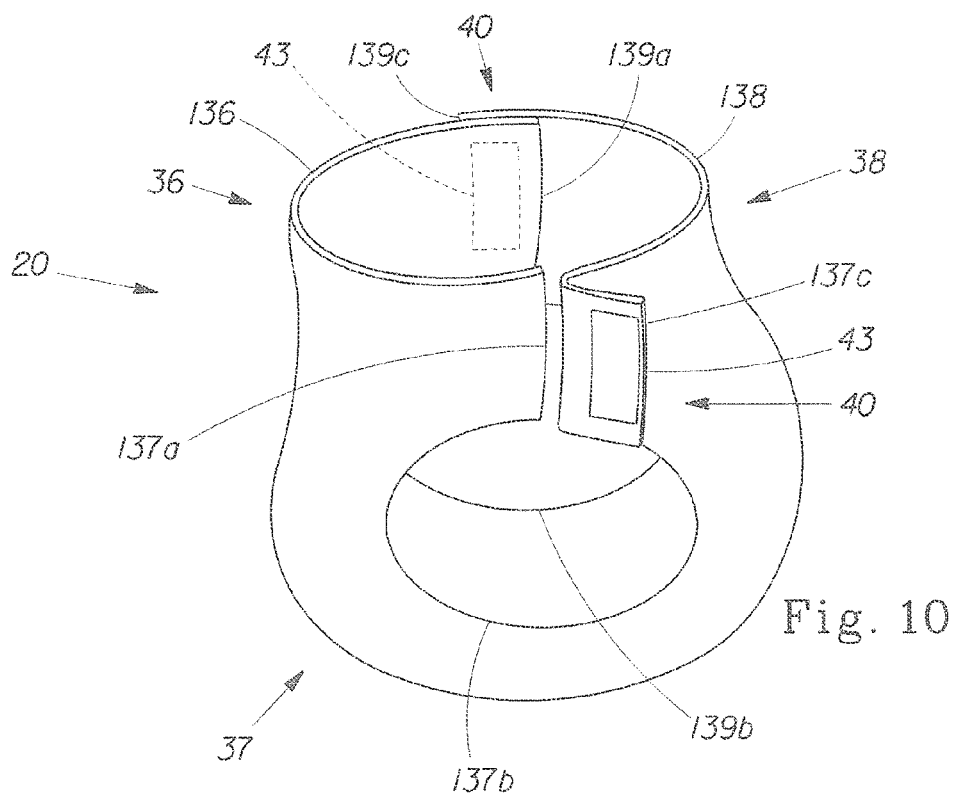
FIG. 10 is a perspective view of an exemplary disposable absorbent article 20, which is shown in its relaxed, contracted state, i.e., with the contraction induced by elastic members.

An example of refastenable side seams 40 is shown in FIG. 10. In this embodiment, a primary fastening component 43 is disposed on the interior of the disposable absorbent article 20 in the second waist region 38 adjacent to the portion 137c of the first side edge and another primary fastening component 43 is disposed on the interior of the disposable absorbent article 20 in the second waist region adjacent to the portion 139c of the second side edge. The portion 137c of the side edge is shown in an open condition, such as prior to closing and fastening or after being reopened. The portion 139c of the opposing side edge is shown fastened, i.e., forming a pants configuration. In FIG. 10, the second waist region 38 overlaps the first waist region 36 when they are fastened together. Alternatively, the primary fastening components 43 may be disposed on the interior of the article 20 in the first waist region 36 such that the first waist region 36 overlaps the second waist region 38 when they are fastened together. In addition, the primary fastening components 43 may be disposed on the exterior of the article 20 rather than on the interior.

The primary fastening component may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface.

As described in more detail below, the primary fastening component may also interact with a discrete mating fastening component. For example, a mechanical primary fastening component containing hooks may engage with a discrete mating fastening component containing loops. Similarly, an adhesive primary fastening component may adhere to a discrete mating fastening sheet that is specifically selected for good adhesion. Also similarly, a cohesive primary fastening component may cohere to a mating cohesive fastening component. Each of the fastening components may have any suitable shape, such as rectangular, circular, ovaloid, undulating, etc. The shape may be chosen according to various criteria, such as to maximize or minimize the area of the fastening component, to impart a particular appearance to the fastening component, to distribute the stresses and forces to which the fastening component is subjected when the article is worn in a particular way, etc.

Figure 11:
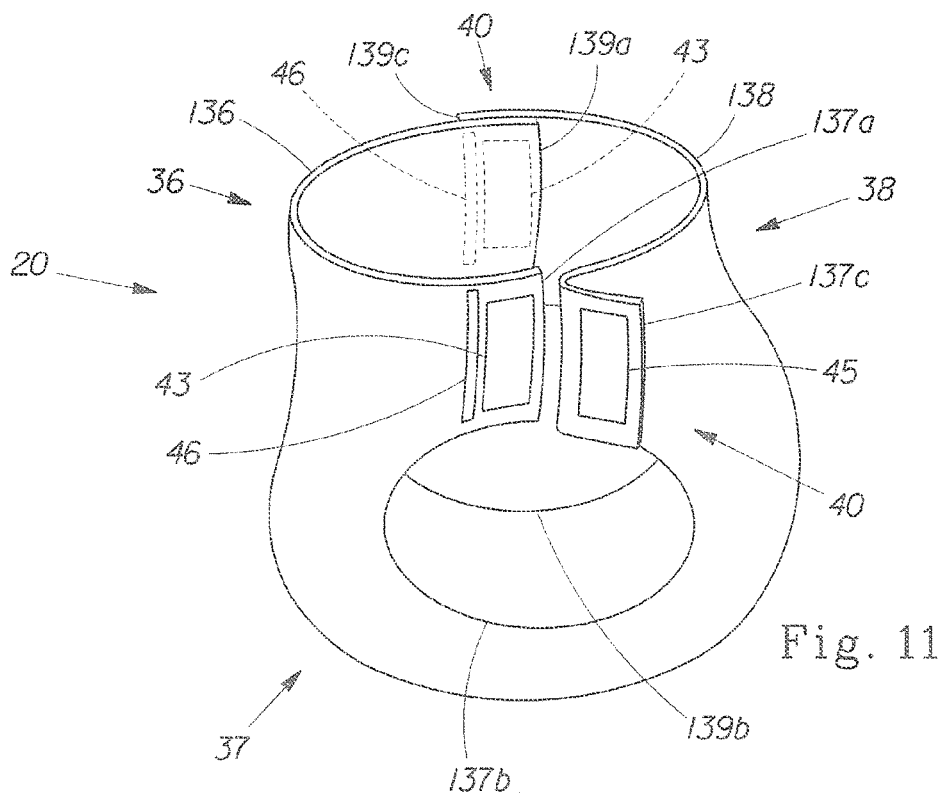
FIG. 11 is another perspective view similarly oriented.

Another example of refastenable side seams is shown in FIG. 11. In this embodiment, the primary fastening components 43 are disposed on the exterior of the disposable absorbent article 20 in the first waist region adjacent to the portions 137a and 139a of the respective side edges. Discrete mating fastening components 45 are correspondingly disposed on the interior of the article 20 in the second waist region 38 adjacent to the portions 137c and 139c of the respective side edges. In addition, secondary fastening components 46 are disposed laterally adjacent to the primary fastening components 43.

When both primary fastening components and discrete mating fastening components are present, their disposition relative to the interior and exterior of the disposable absorbent article is generally interchangeable, i.e., they may be disposed as shown in FIG. 11 or the primary fastening component may be disposed interiorly and the mating fastening component may be disposed interiorly. Similarly, their disposition relative to the first waist region and the second waist region is generally interchangeable, i.e., they may be disposed such that the second waist region 38 overlaps the first waist region 36 when they are fastened together as shown in FIG. 11 or they may be disposed such that the first waist region 36 overlaps the second waist region 38 when they are fastened together. In addition, the secondary fastening components may be disposed adjacent to the primary fastening components and on the same surface as the primary fastening components, as shown in FIG. 11, or may be disposed on a mating surface and/or adjacent to a discrete mating fastening component. In general, as is apparent from the above description, the initial disposition(s) of the primary fastening component(s) is (are) not critical, so long as the opposing waist regions can be fastened together in an overlapped configuration to sandwich the fastening component(s) between them.

Figure 12:
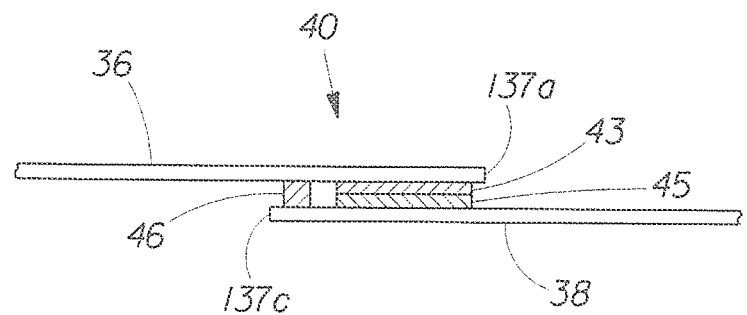
FIG. 12 is a cross sectional view of the refastenable side seam 40 shown in an open condition in FIG. 11, showing the side seam in a fastened condition.

In the exemplary embodiment shown in FIG. 12, each of the secondary fastening components serves to fasten the overlapping portions of the waist regions together adjacent to the releasable attachment formed by the adjacent primary and the mating fastening components. When disposed between the primary fastening component 43 and the portion 137c of the side edge that exteriorly overlaps in the fastened side seam 40, as shown in FIG. 12, the secondary fastening component may restrict and/or prevent direct lateral access to the primary fastening component and thereby help protect against the opening of the side seams by a child who is wearing the disposable absorbent article. In order to enhance this protection, the secondary fastening component may overlap the primary fastening component in addition to being disposed between it and the exteriorly overlapped side edge, thereby eliminating any laterally extending gap between the two, into which a finger could be inserted to pry the overlapping waist region loose from the overlapped waist region. Alternatively or in addition, a secondary fastening component may be disposed between the side edge that is interiorly overlapped and the primary fastening component, i.e., laterally symmetrically opposite the secondary fastening component shown in FIG. 12.

Figure 13:
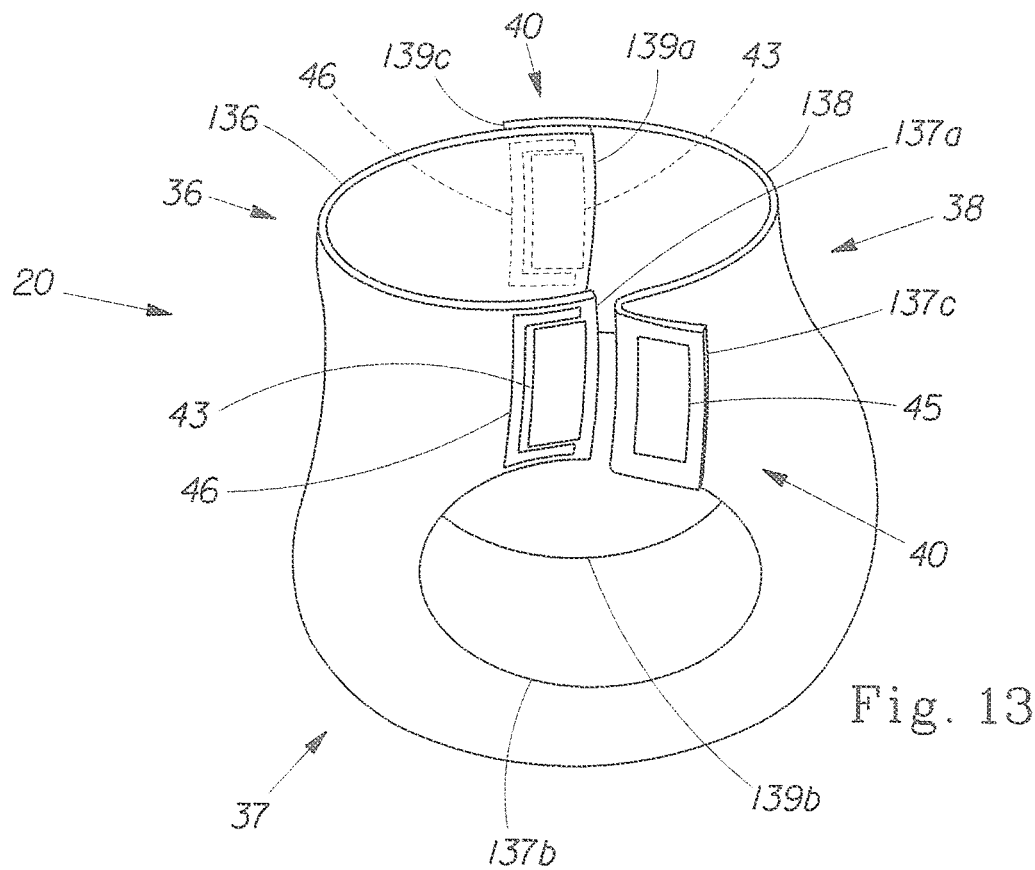
FIG. 13 is another perspective view oriented similarly to the views of FIG. 10 and FIG. 11, showing an alternative form of secondary fastening component.

Alternatively or in addition, a secondary fastening component may be disposed between the primary fastening component and the adjacent waist edge and/or between the primary fastening component and the crotch region. Such a longitudinally adjacent disposition of the secondary fastening component relative to the primary fastener in the fastened side seam may more effectively restrict the access to the primary fastener than only a laterally adjacent disposition. Also, the secondary fastening component may be disposed both laterally adjacent and longitudinally adjacent to the primary fastener. For example, the secondary fastening component 46 shown in FIG. 13 extends around three sides of the primary fastening component 43 so as to be disposed between the primary fastening component and each of the exteriorly overlapping side edge portion 137c, the adjacent waist edge 136, and the crotch region 37, when the side seam is fastened. As an alternative to a continuously extending secondary fastening component like that shown in FIG. 13, more than one discrete secondary fastening component and/or a segmented secondary fastening component may be provided. For example, a discrete laterally adjacent longitudinally extending secondary fastener like that in FIG. 11 may be provided in combination with one or more discrete longitudinally adjacent laterally extending secondary fastener(s) to form an overall secondary fastening component pattern similar to that formed by the continuous secondary fastening component of FIG. 13.

The secondary fastening component may be formed of any material that is suitable for the primary fastening component. In some embodiments, the secondary fastening components may be formed of a different material from the primary fastening component in order to take advantage of the unique properties of different materials. For example, a mechanical fastener may be used for the primary fastening component in order to provide sufficient shear strength when fastened to resist the hoop forces to which the waist regions are subjected when the disposable absorbent article is worn. An adhesive may be used for the corresponding secondary fastening component because the mechanical fastener resists substantially all of the shear forces and the only force exerted on the secondary fastening component is a peel force that is applied when the caregiver desires to gain access to the primary fastening component. The secondary fastening component is preferably refastenable after being opened, so that it can continue to be used to restrict access to the primary fastening component after the latter has been opened and refastened.

Additional details of exemplary refastenable side seams are provided in co-pending and commonly assigned U.S. patent application Ser. No. 10/815,918 filed on Apr. 1, 2004 in the name of Vargo et al, incorporated by reference herein.

As noted above, the secondary fastening components may be formed of any material that is suitable for the primary fastening components and/or may be formed of a different material from the primary fastening components in order to take advantage of the unique properties of different materials. In addition, the secondary fastening components may be formed by bonding, sealing, or otherwise attaching the opposing waist regions together adjacent to their common side edges, e.g., if it is desired to configure the disposable absorbent article as a pair of training pants and to provide the refastenable side seam in the form of a cinching feature. For example, the secondary fastening components may be located such that the fit around the waist of the intended size of wearer is relatively loose to provide a desired degree of access for the inspection of the interior of the article. The refastenable primary fastening components may then be used to cinch the overlapping waist region to achieve the desired fit on the wearer. Whenever it is desired to inspect the interior of the article, the primary fastening component may be unfastened and subsequently refastened after the inspection is completed. Additionally, the secondary fastening component that is formed by bonding, sealing, or otherwise attaching the waist regions together may be frangible, such that it can be unfastened to detach the waist regions from each other, e.g., to enlarge the size of the waist opening and/or for the removal of the article after use. In such an embodiment, the refastenable primary fastening component may still be used to fasten the waist regions together and may still be opened for the inspection of the interior of the article and/or for the removal of the article after use.

Several forms of refastenable side seams, the fastening components forming them, and the materials that are suitable for forming them are described in U.S. Patent Application Publication US 2003/0060794 published on 27 Mar. 2003 in the name of Olson. Processes for forming refastenable side fasteners and for protecting them during manufacturing and packaging are described in U.S. Pat. No. 6,428,526 issued on 6 Aug. 2002 in the name of Heindel et al. Among several alternatives, such side seams, fastening components, materials, and processes may be used to produce the disposable absorbent articles of the present disclosure.

Figure 14A:
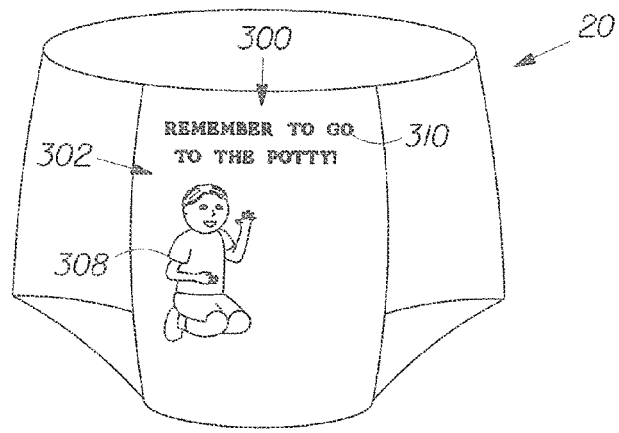
FIG. 14a is a front perspective view of an absorbent article having appearing graphics in an initial state.
Figure 14B:
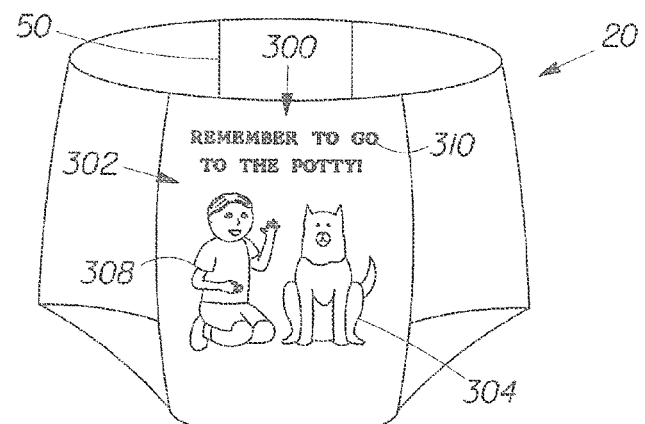
FIG. 14b is a front perspective view of the absorbent article of FIG. 14a showing a first appearing graphic in a subsequent state.
Figure 14C:
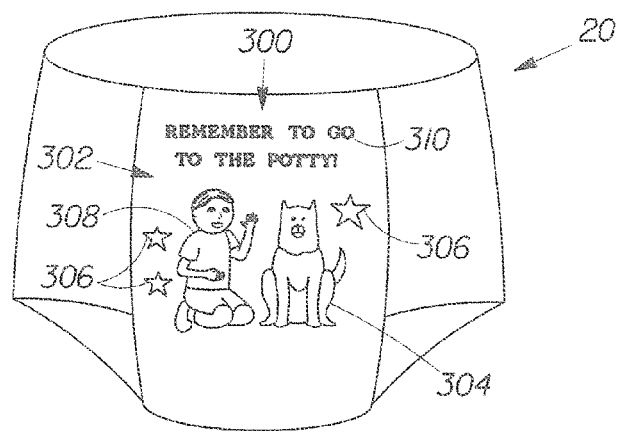
FIG. 14c is a front perspective view of the absorbent article of FIG. 14a with both a first and a second appearing graphic in subsequent states.

The absorbent article 20 may further include graphics 300 which facilitate toilet training, as illustrated in FIGS. 14a-c. In the exemplary embodiment, the graphics 300 include a permanent graphic 302, a first appearing graphic 304, and a second appearing graphic 306. The permanent graphic 300 may include a character image 308 resembling a boy and a text graphic 310 including words forming a message, such as "Remember to go to the potty!" As illustrated, the boy in the character image 308 is kneeling on the ground and the text graphic 310 is located above the character image 308. While the permanent graphic 302 is illustrated as including the character image 308, it will be appreciated that the permanent graphic 302 may include other graphics such as an object, design, or pattern. Furthermore, character images other than a boy may be provided, such as a girl, an animal (which may be anthropomorphic), a cartoon character, and the like. Still further, additional or alternative text may be provided in the permanent graphic 300.

The first appearing graphic 304 is illustrated as a character image that may be associatively correlated to the permanent graphic 302. In the illustrated embodiment, the first appearing graphic 304 is in the form of a dog sitting next to the boy character image 308, with the boy character image 308 appearing to pet the dog. As with the permanent graphic 302, the first appearing graphic 304 may be in the form of a different character other than the dog, or may be in the form of something other than a character, such as an object, design, pattern, background color, or text.

The second appearing graphic 306 is illustrated as an object image that may be associatively correlated to the permanent graphic 302 and the first appearing graphic 304. In the illustrated embodiment, the second appearing graphic 306 is in the form of a plurality of stars located proximate the permanent graphic 302 and the first appearing graphic 304. The second appearing graphic 306 may be in the form of a different object other than a plurality of stars, or may be in the form of something other than an object, such as a character, design, pattern, background color, or text. Still further, while the exemplary embodiment shows three stars, fewer or less than three objects may be provided as the second appearing graphic 306.

As noted above, the permanent, first appearing, and second appearing graphics 302, 304, 306 may be associatively correlated to one another to form a scene. Accordingly, the graphics may relate to a common theme or story line. While the illustrated embodiment shows a scene including a boy, dog, and star images, other scenes may be provided. For example, the scene may include images of a girl, a flower, and a rainbow, or a cat, a cow, and a moon, as but two examples. Similarly, the graphics may include images which children already associate with each other, such as a cartoon or popular entertainment character and the typical friends, partners, or objects that appear with the main character. When such familiar images are used, the child will expect the second character or item that is usually associated with the partial scene to appear, thereby maintaining the child's interest and encouraging him or her to complete a toilet training task, such as staying dry, until the scene is complete.

Alternatively or additionally, the graphics may be associatively correlated based on their proximity to one another. The graphics may include multiple separate images that form a complete scene having multiple interrelated objects or characters as noted above. Alternatively, the multiple graphics may build a unitary final image. In this case, for example, the permanent image may be of an object or character that is intrinsically or inherently incomplete, such as a partial drawing like a flower stem without a flower. The appearing graphics may be images of additional parts of the flower, such as flower petals, leaves, and the like. Accordingly, the child will remain interested in the toilet training task at least until completion of the final, composite image.

The graphics may be in the form of any visual representation that attracts the attention of, or is otherwise identifiable by, the wearer. The graphics may include one or more icons, which may comprise, but are not limited to, pictorial symbols, photographs, drawings, cartoons, and logos. For example, the icons may be provided as drawings of a child or an anthropomorphic image of an animal using the article 20. Similarly, the icons may include well-known cartoon characters or brand logos, or characters specifically created to be associated with the article. The icons may further include symbols, such as arrows, to indicate motion, movement, or directionality.

The graphics may be arranged in any manner as long as they are viewable by the wearer. The graphics may include a single icon or a series of icons. If a series of icons is provided, each icon may be different. Different icons may be complementary to one another, in that they are related to the same concept or activity, or incorporate a common visual element (such as a similar appearance, color, or theme). The icons may be arranged in any suitable fashion, such as, but not limited to, vertically, horizontally, diagonally, circular, arcs, and combinations thereof.

The graphics may optionally include a character image that can increase a user's interest in the product. The term "character image" is used herein to refer to a graphic containing an anthropomorphic image, and in particular an image having or suggesting human form or appearance which ascribes human motivations, characteristics or behavior to inanimate objects, animals, natural phenomena, toys, cartoon characters, or the like. The character image may be associated with popular characters in the media, advertising or well known in a particular culture. Ideally they are characters that the user, particularly if a child, cares about and wants to identify with.

The graphics disclosed herein are particularly suited for absorbent articles intended for use by children. Accordingly, the exemplary images illustrated herein may be cognitively functional to a pre-literate child. While the graphics may include text, the primary form of communication may be symbols, icons, or other markings other than words, so that a pre-literate child may comprehend and follow the instructions or other information indicated by the graphics.

As used herein, the terms "pre-literate" and "incapable of reading" are used interchangeably to mean the inability of a child to correctly understand, comprehend and follow prompts written in a language that the child can speak without assistance of a caregiver. The ability of a child to recognize letters and/or read one or two isolated words still means that the child is "incapable of reading" since he or she is unable to understand, comprehend and follow such written prompts, without assistance. However, this definition of "incapable of reading" does not exclude the child from being able to understand, comprehend and follow visual prompts which are presented in the form of drawings, icons, symbols, gestures, cartoons and the like. Furthermore, while the disclosed embodiments are capable of being understood by a pre-literate child, it is not necessary for the images to be understood at this level.

The first and second appearing graphics 304, 306 may appear at different time intervals to build interest and encourage the child not to urinate in the article 20. Use of appearing graphics allows a caregiver to explain the appearance of a new graphic for a reward, and therefore a more positive approach to toilet training may be taken. For example, the appearing graphic may be viewed as a reward for the child staying dry. Accordingly, each of the first and second appearing graphics 304, 306 has an initial state, in which the graphic is transparent, translucent, or relatively less visible, and a subsequent state, in which the graphic is at least semi-opaque or otherwise relatively more visible. The first appearing graphic 304 may change from the initial state to the subsequent over a first time period, such as, for example, approximately one hour. The second appearing graphic 306 changes from the initial state to the subsequent state over a second time period that may be different from the first time period, such as approximately two hours. Accordingly, the child is initially encouraged by the appearance of the first appearing graphic 304 and learns to anticipate and appreciate the appearance of the second appearing graphic 306 at a later time.

The first and second appearing graphics 304, 306 may become visible at either a uniform or a variable rate. For example, the graphics may appear slowly or gradually over time, such as substantially at the same rate over a period of time such as approximately one hour or approximately two hours. Alternatively, the graphics may appear at a variable or non-uniform rate. For example, the graphics may show no change in visibility for an initial period of time followed by a period of more rapid change in visibility. As but one example, the graphics may remain substantially hidden, obscured, or less visible for a period of approximately 50 minutes and then more rapidly change to a more visible state over a period of approximately 10 minutes. Furthermore, while the exemplary second time period of two hours is twice the exemplary first time period of one hour, the time periods need not be related by any relative ratio. Instead, the time periods may include any suitable time interval. In addition, while the exemplary embodiment illustrates first and second appearing graphics 304, 306, a third or more appearing graphics may be provided having different time periods for changing from the initial to the subsequent state without departing from the scope of this disclosure.

The appearing graphics 304, 306 may become less visible when subjected to liquid such as urine, thereby to discourage a child from urinating in the article 20. Accordingly, the appearing graphics 304, 306 may be positioned or otherwise placed in liquid communication with the absorbent assembly 28, meaning that liquid such as urine is capable of moving between the appearing graphics 304, 306 and the absorbent assembly 28 under ordinary use conditions. Consequently, when a child wets the absorbent article 20, liquid is communicated to the appearing graphics 304, 306, whereupon the appearing graphics dissolve, change color, disappear, or the like. For example, should the first appearing graphic 304 as shown in FIG. 14b, or the first and second appearing graphics 304, 306 as shown in FIG. 14c, be in the subsequent state and hence visible, the appearing graphics 304, 306 will disappear upon contact with urine, leaving the permanent graphic 302 as shown in FIG. 14a.

The permanent graphic 302, as well as the first and second appearing graphics 304, 306 when in the subsequent state, are viewable from an exterior of the article 20. Specifically, the graphics are viewable at the exterior surface of the backsheet 26. Accordingly, the graphics may be disposed on the backsheet 26, the absorbent assembly 28, or a layer located therebetween. For purposes of this disclosure, should a separate, intermediate layer of material be located between the backsheet 26 and the absorbent assembly 28, the intermediate layer will be considered to be associated with at least one of the backsheet 26 and the absorbent assembly 28, and therefore a graphic disposed on such an intermediate layer is considered to be disposed on at least one of the backsheet 26 and the absorbent assembly 28.

Figure 15A:
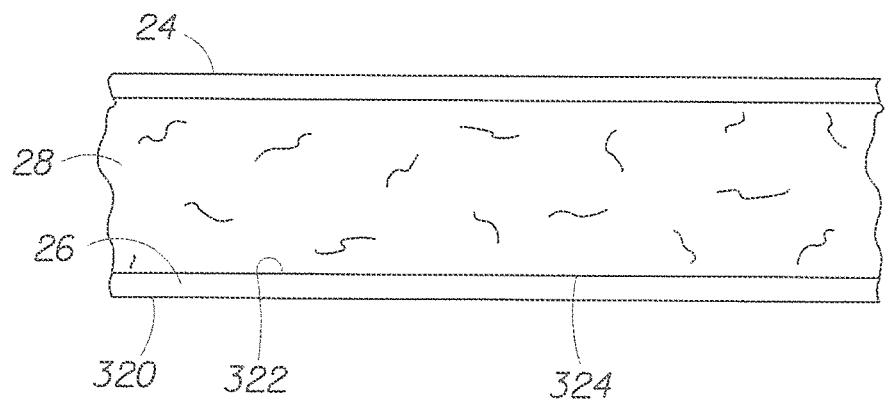
FIG. 15a is a partial section view of an absorbent article with a single layer backsheet.
Figure 15B:
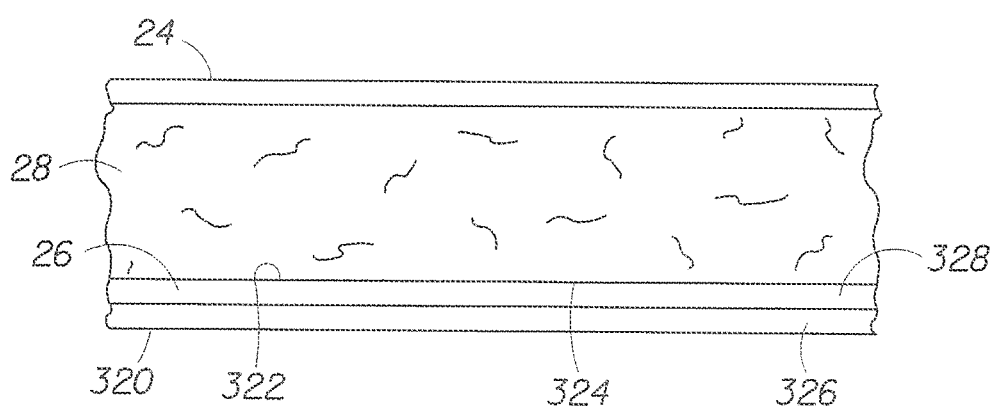
FIG. 15b is a partial section view of an absorbent article with a double layer backsheet.

Various placements of the graphics 302, 304, 306 may be better understood with reference to the partial section views of absorbent articles that are shown in FIG. 15a and FIG. 15b. The various layers of the illustrated embodiments can be secured together using adhesives, thermal bonds, mechanical bonds, or other means known to those skilled in the art.

FIG. 15a illustrates a partial section view of an absorbent article having an absorbent assembly 28 sandwiched between a backsheet 26 and a topsheet 24. The illustrated backsheet 26 consists of a single layer having an exterior surface 320 and an opposite interior surface 322. The permanent and appearing graphics 302, 304, 306 may be disposed on the backsheet 26, which includes on either surface 320 or 322 of the backsheet, on an exterior surface 324 of the absorbent assembly 28, or between the absorbent assembly and the backsheet. The backsheet 26 is preferably formed of a material that is liquid impermeable. The permanent graphic 302 and appearing graphics 304, 306 need not be located in the same position or on the same substrate.

FIG. 15b illustrates a partial section view of another absorbent article having an absorbent assembly 28 sandwiched between a backsheet 26 and a topsheet 24. The illustrated backsheet 26 consists of a two-layer composite comprising an outer layer 326 and an inner layer 328. The backsheet 26 has an exterior surface 320 and an opposite interior surface 322. The permanent and appearing graphics 302, 304, 306 may be disposed on the backsheet 26, which includes, in particular, on the exterior surface 320, on the interior surface 322, between the outer and inner layers 326, 328, on either or both facing surfaces of the outer and inner layers 326, 328, on the exterior surface 324 of the absorbent assembly 28, or between the absorbent assembly and backsheet.

Various types of mechanisms may be used to obtain the desired time periods between the initial and subsequent states of the appearing graphics 304, 306. For example, the graphics 304, 306, may be formed by a chemical composition that exhibits different characteristics, such as different colors, when subjected to altered environmental conditions. A dye, such as methylene blue, may be used which is colorless when in a reduced state but which turns blue in an oxidized state. To reach the oxidized state, the dye must be exposed to oxygen. Accordingly, if the appearing graphics 304, 306 are formed of methylene blue, they will initially be colorless but subsequently turn blue (and visible) when oxidized by sufficient exposure to atmosphere. Initiation of the oxidation may be controlled by sealing the appearing graphics 304, 306 prior to use, such as by covering with a membrane or plastic that is removed approximately at the time the article is first worn. The methylene blue dye has the added benefit of being liquid soluble, and therefore may be flushed to the absorbent assembly 28 or other area of the article when exposed to urine, thereby causing the appearing graphics 304, 306 to disappear, become obscured, or otherwise be less visible.

Alternatives to the foregoing dye composition may be used to effect an appearing graphic. Inks or dyes that change appearance when subjected to different temperatures, conductivity or resistivity, or other surrounding conditions may be used. Still further, rather than a special ink or dye, a mechanical structure may be provided that controls flow of ink from an obscured location to a location viewable from the exterior of the article may be used. The ink or dye may be stored in a reservoir that is at least initially not viewable from an exterior of the article. A filter, capillary tube, or other mechanical structure may control flow of the dye to an exteriorly visible location, effectively creating a time release of the dye. The appearing graphic may use electrical means to measure time periods and/or release ink or other graphic material. For example, a simple circuit for measuring time may be provided, thereby equipping the article with an electronic timer that may be powered by a small battery or other power source. The timer circuit may generate an electronic signal indicating the desired time for releasing ink or the like from a storage location.

The absorbent article 20 may include structure for providing feedback to a child using multiple senses, thereby more clearly indicating the desired behavior during toilet training. The article 20, for example, may include at least the first appearing graphic 304 to provide positive encouragement to stay dry and also at least wetness sensation member, such as member 50, to provide negative reinforcement or otherwise inform the child or caregiver that an accident has occurred. The appearing graphic 304 generates a visual cue received by the sense of sight, while the wetness sensation member 50 provides a tactile signal received by the child's sense of touch. By providing feedback receivable by multiple senses, the child is more apt to learn and remember the desired behavior for toilet training.

Any of the above described product features can be combined in any desired combination. For example, product features including (but not limited too), a wetness sensation member (either permanent or removable), refastenable sides, and appearing graphics, may all be combined in a single disposable pant like garment product offering. In other variations, only some of these features may be included, and they may offered in any desired combination or sub-combination. Additionally, variations of products may be combined into a single package to provide a potty training kit or system, and particular suggestions of model systems may be provided. As an example, a series of pant like garments may be include in a single potty training system kit. Some of the products might have a wetness sensation liner, and others may not. In such an example, other product features (such as refastenable sides and appearing graphics) may be included in all products in the kit, in none of them, or in some products in any desired combination.

All documents cited in the Detailed Description of the Invention are, in relevant part, incorporated herein by reference; the citation of any document is not to be construed as an admission that it is prior art with respect to the present invention.

While particular embodiments and/or individual features of the present disclosure have been illustrated and described, it would be obvious to those skilled in the art that various other changes and modifications can be made without departing from the spirit and scope of the disclosure. Further, it should be apparent that all combinations of such embodiments and features are possible and can result in preferred executions of the disclosure. Therefore, the appended claims are intended to cover all such changes and modifications that are within the scope of this disclosure.

What is claimed is:

1. An absorbent article for wearing about a lower torso of a wearer and having a longitudinal axis, two laterally opposed article side edges extending between a laterally extending first waist end edge in a first waist region and a laterally extending second waist end edge in a second waist region, and a crotch region interposed therebetween, the disposable absorbent article comprising:
   backsheet;
   a topsheet joined to the backsheet and having a body-facing surface;
   an absorbent assembly disposed intermediate the backsheet and the topsheet;
   at least one wetness sensation member positioned to closely contact a wearer's skin during use, the wetness sensation member including a permeable layer, and an impermeable layer disposed in face-to-face arrangement with the permeable layer, wherein urine deposited onto the wetness sensation member can penetrate through the permeable layer in a z direction to the impermeable layer and wherein the impermeable layer prevents urine from passing completely through the member in the z direction and supports movement of urine in an x-y plane such that the wearer's awareness of urination is enhanced;
   at least a first appearing graphic disposed on one of the backsheet and absorbent assembly and viewable at the exterior surface, the first appearing graphic having an initial state in which the first appearing graphic is less visible and, after a first period of time, a subsequent state in which the first appearing graphic is more visible; and
   a second appearing graphic, different from the first appearing graphic, disposed on one of the back sheet and absorbent assembly and viewable at the exterior surface, the second appearing graphic having an initial state in which the second appearing graphic is less visible and, after a second period of time different from the first period of time, a subsequent state in which the second appearing graphic is more visible.

2. The absorbent article of claim 1, in which the first and second appearing graphics are less visible upon exposure to liquid.

3. The absorbent article of claim 1, in which the first and second appearing graphics comprise liquid-soluble ink.

4. The absorbent article of claim 1, in which the first appearing graphic comprises a character image and the second appearing graphic comprises an object image, wherein the character image and the object image are related by a common story line.

5. The absorbent article of claim 1, in which the first appearing graphic is associatively correlated to the second appearing graphic.

6. The absorbent article of claim 5, in which the first and second appearing graphics comprise parts of a unitary image.

7. The absorbent article of claim 5, in which the first and second appearing graphics comprise first and second separate images.

8. The absorbent article of claim 5, further comprising a permanent graphic disposed on one of the back sheet and absorbent assembly and viewable at the exterior surface, wherein the permanent graphic is associatively correlated to the first and second appearing graphics.

* * * * *